(12) United States Patent
Hioki

(10) Patent No.: US 11,324,671 B2
(45) Date of Patent: May 10, 2022

(54) INTERFERENCE PIGMENT, AND COSMETIC PREPARATION, COATING MATERIAL, INK, AND RESIN COMPOSITION EACH CONTAINING SAME

(71) Applicant: Nippon Sheet Glass Company, Limited, Tokyo (JP)

(72) Inventor: Masahiro Hioki, Mie (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 0 days.

(21) Appl. No.: 15/578,605

(22) PCT Filed: May 31, 2016

(86) PCT No.: PCT/JP2016/066034
§ 371 (c)(1),
(2) Date: Nov. 30, 2017

(87) PCT Pub. No.: WO2016/194902
PCT Pub. Date: Dec. 8, 2016

(65) Prior Publication Data
US 2018/0133116 A1     May 17, 2018

(30) Foreign Application Priority Data

Jun. 1, 2015    (JP) .............................. JP2015-111637

(51) Int. Cl.
*A61K 8/02*     (2006.01)
*A61K 8/25*     (2006.01)
(Continued)

(52) U.S. Cl.
CPC .......... *A61K 8/0266* (2013.01); *A61K 8/0229* (2013.01); *A61K 8/19* (2013.01);
(Continued)

(58) Field of Classification Search
CPC ... A61K 8/19; A61K 8/25; A61K 8/26; A61K 8/29; A61K 8/0229; A61K 8/0266;
(Continued)

(56) References Cited

U.S. PATENT DOCUMENTS

| | | | |
|---|---|---|---|
| 4,954,176 A | | 9/1990 | Minohara et al. |
| 5,002,608 A | * | 3/1991 | Fujiwara ............... C09C 1/0015 |
| | | | 106/415 |

(Continued)

FOREIGN PATENT DOCUMENTS

| | | |
|---|---|---|
| JP | 1-108267 | 4/1989 |
| JP | 4-193725 | 7/1992 |

(Continued)

*Primary Examiner* — Pegah Parvini
*Assistant Examiner* — Ross J Christie
(74) *Attorney, Agent, or Firm* — Hamre, Schumann, Mueller & Larson, P.C.

(57) ABSTRACT

The present invention provides an interference pigment that develops interference colors even on light-colored bases. An interference pigment 1 of the present invention includes: a flaky inorganic substrate 10; a transparent metal layer 20 that coats the inorganic substrate 10; and a metal oxide layer 30 that coats the metal layer 20.

13 Claims, 1 Drawing Sheet

(51) Int. Cl.
| | |
|---|---|
| A61Q 1/04 | (2006.01) |
| A61Q 1/06 | (2006.01) |
| C09D 5/29 | (2006.01) |
| C09D 11/037 | (2014.01) |
| C08K 9/02 | (2006.01) |
| C09D 11/322 | (2014.01) |
| A61K 8/26 | (2006.01) |
| C09D 201/00 | (2006.01) |
| C08L 101/00 | (2006.01) |
| C09D 7/40 | (2018.01) |
| C09C 1/00 | (2006.01) |
| C09C 1/28 | (2006.01) |
| A61K 8/19 | (2006.01) |
| A61K 8/29 | (2006.01) |
| C09C 3/06 | (2006.01) |

(52) U.S. Cl.
CPC .................. *A61K 8/25* (2013.01); *A61K 8/26* (2013.01); *A61K 8/29* (2013.01); *A61Q 1/04* (2013.01); *A61Q 1/06* (2013.01); *C08K 9/02* (2013.01); *C08L 101/00* (2013.01); *C09C 1/0015* (2013.01); *C09C 1/0033* (2013.01); *C09C 1/0078* (2013.01); *C09C 1/28* (2013.01); *C09C 3/063* (2013.01); *C09D 5/29* (2013.01); *C09D 7/40* (2018.01); *C09D 7/70* (2018.01); *C09D 11/037* (2013.01); *C09D 11/322* (2013.01); *C09D 201/00* (2013.01); *A61K 2800/436* (2013.01); *C09C 2200/1008* (2013.01); *C09C 2200/1025* (2013.01); *C09C 2200/1029* (2013.01); *C09C 2200/304* (2013.01); *C09C 2200/306* (2013.01)

(58) Field of Classification Search
CPC .. A61K 2800/436; C09C 1/28; C09C 1/0015; C09C 1/0033; C09C 1/0078; C09C 3/063; C09C 2200/1008; C09C 2200/1025; C09C 2200/1029; C09C 2200/304; C09C 2200/306; C09D 5/29; C09D 7/40; C09D 7/70; C09D 11/037; C09D 11/322; C09D 201/00; A61Q 1/04; A61Q 1/06; C08L 101/00; C08K 9/02
See application file for complete search history.

(56) References Cited

U.S. PATENT DOCUMENTS

| | | | |
|---|---|---|---|
| 5,436,077 A | 7/1995 | Matsuba et al. | |
| 5,624,486 A | 4/1997 | Schmid et al. | |
| 6,287,695 B1 | 9/2001 | Kaupp et al. | |
| 6,632,275 B1 | 10/2003 | Schoen et al. | |
| 6,747,073 B1 | 6/2004 | Pfaff et al. | |
| 6,794,037 B2 * | 9/2004 | Zimmermann | C09C 1/0015 106/415 |
| 6,800,125 B2 * | 10/2004 | Zimmermann | C09C 1/0015 106/403 |
| 6,821,333 B2 * | 11/2004 | Zimmermann | B82Y 30/00 106/403 |
| 6,936,348 B1 | 8/2005 | Yanagase | |
| 8,500,901 B2 * | 8/2013 | Rueger | C09C 1/0051 106/415 |
| 2003/0051634 A1 | 3/2003 | Takahashi | |
| 2004/0112252 A1* | 6/2004 | Zimmermann | B82Y 30/00 106/415 |
| 2004/0115432 A1* | 6/2004 | Zimmermann | C09C 1/0015 428/403 |
| 2007/0251424 A1* | 11/2007 | Handrosch | C04B 20/12 106/472 |
| 2007/0275244 A1* | 11/2007 | Handrosch | A61K 8/0266 428/403 |
| 2008/0124559 A1 | 5/2008 | Fujiwara et al. | |
| 2008/0279796 A1* | 11/2008 | Handrosch | C09C 1/0015 106/418 |
| 2008/0280150 A1* | 11/2008 | Jones | C01G 49/0018 428/450 |
| 2009/0311209 A1* | 12/2009 | Bujard | A61K 8/25 424/63 |
| 2010/0011992 A1* | 1/2010 | Bujard | B82Y 30/00 106/439 |
| 2010/0116169 A1* | 5/2010 | Kaupp | C03C 3/093 106/31.9 |
| 2010/0129412 A1* | 5/2010 | Kitamura | A61K 8/19 424/401 |
| 2010/0227181 A1* | 9/2010 | Kitamura | C09C 1/0015 428/457 |
| 2010/0249304 A1* | 9/2010 | Kitamura | C09C 1/0015 524/403 |
| 2012/0301554 A1* | 11/2012 | Kniess | C09D 7/70 106/439 |

FOREIGN PATENT DOCUMENTS

| | | |
|---|---|---|
| JP | 6-032995 | 2/1994 |
| JP | 7-000759 | 1/1995 |
| JP | 7-258579 | 10/1995 |
| JP | 10-088026 | 4/1998 |
| JP | 2001-031421 | 2/2001 |
| JP | 2002-516375 | 6/2002 |
| JP | 2002-535435 | 10/2002 |
| JP | 2003-089758 | 3/2003 |
| JP | 2004-510013 | 4/2004 |
| JP | 2004-522853 | 7/2004 |
| JP | 2005-187782 | 7/2005 |
| JP | 2006-516154 | 6/2006 |
| JP | 2008-546880 | 12/2008 |
| JP | 2010-538096 | 12/2010 |
| WO | 02/24818 | 3/2002 |
| WO | 02/42522 | 5/2002 |
| WO | 2004/055118 | 7/2004 |
| WO | 2006/068255 | 6/2006 |
| WO | 2007/054379 | 5/2007 |
| WO | 2008/122420 | 10/2008 |
| WO | 2008/130040 | 10/2008 |

\* cited by examiner

INTERFERENCE PIGMENT, AND COSMETIC PREPARATION, COATING MATERIAL, INK, AND RESIN COMPOSITION EACH CONTAINING SAME

TECHNICAL FIELD

The present invention relates to an interference pigment; and a cosmetic, a paint, an ink, and a resin composition including the interference pigment.

BACKGROUND ART

As metallic pigments, flaky aluminum powders, flaky natural mica powders and flaky graphite powders coated with metal oxide (e.g., titanium dioxide, iron oxide), and iron oxide particles mainly composed of α-iron oxide crystal particles have been known conventionally. These metallic pigments have the property of glittering by reflecting light from the surfaces thereof, and are used as materials for paints, inks, resin compositions for molding, and cosmetics.

For example, JP H01(1989)-108267 A (Patent Document 1) proposes, as one of interference pigments containing metal, an interference pigment that includes: a ceramic flaky substrate; a titanium dioxide layer formed on the entire surface of the substrate; and metallic bright parts formed on the surface of the titanium dioxide layer. In the interference pigment, the metallic bright parts are dotted like islands on the surface of the titanium dioxide layer in the ratio of from 0.05 to 95% of the total surface area of the titanium dioxide layer. As another example, JP 2003-089758 A (Patent Document 2) proposes a high-chromatic flaky pigment with good colorability exhibiting interference colors in which a substrate of metal pigment is subsequently coated with a metal oxide and a semi-transparent thin metal film. As still another example, JP H06(1994)-32995 A (Patent Document 3) proposes chromatic glittering powder in which a platy substrate (flaky glass or mica coated with iron oxide, metal powder (aluminum or nickel), metal foil, or metal) is coated with titanium dioxide.

JP H07(1995)-759 B (Patent Document 4) proposes chromatic glittering powder in which a substrate (flaky glass or mica coated with iron oxide, metal powder (aluminum, nickel), metal foil, or metal) is alternately coated with silicon oxide and titanium dioxide.

JP H07(1995)-258579 A (Patent Document 5) proposes a pigment with strong metallic effects in which a platy substrate (muscovite, talc, glass, phlogopite, or biotite) is subsequently coated with $Al_2O_3$ or $SiO_2$, metal and/or non-selectively absorbing metal oxide, and colorless and/or selectively absorbing metal oxide.

The pigments disclosed in these documents can impart chromatic colors and strong metallic effects to cosmetics, paints, inks, and resin compositions that include these pigments. However, since the substrates of these pigments are either an opaque substrate or a substrate obtained by coating a transparent substrate with a metal film with metallic luster, these pigments have low transparency, and cannot sufficiently develop vivid interference colors.

PRIOR ART DOCUMENTS

Patent Documents

Patent Document 1: JP H01(1989)-108267 A
Patent Document 2: JP 2003-089758 A
Patent Document 3: JP H06(1994)-32995 A
Patent Document 4: JP H07(1995)-759 B
Patent Document 5: JP H07(1995)-258579 A

DISCLOSURE OF INVENTION

Problem to be Solved by the Invention

It has been known conventionally that a transparent substrate coated with titanium oxide can cause light interference between light reflected at the surface of the titanium oxide layer and light reflected at the surface of the substrate, thereby developing vivid interference colors. Since the substrate is transparent, designs can be created by utilizing the base color. Such pigments can develop vivid interference colors when the base color is dark (e.g., black); however, they hardly develop interference colors when the base color is light (e.g., white). This is because when the base color is light, lights other than the light reflected at the surface of the titanium oxide layer and the light reflected at the surface of the substrate, i.e., lights passed through the pigment, are reflected at the base and mixed with the lights causing interference, which makes interference colors less visible. Especially when the substrate is glass, glass is transparent, and the substrate has high transmittance, which makes it difficult to develop interference colors.

The present invention provides an interference pigment that can develop vivid interference colors even on light-colored bases; and a cosmetic, a paint, an ink, and a resin composition including the interference pigment.

Means for Solving Problem

An interference pigment of the present invention includes: a flaky inorganic substrate; a transparent metal layer that coats the inorganic substrate; and a metal oxide layer that coats the metal layer.

A cosmetic of the present invention contains the interference pigment of the present invention.

A paint of the present invention contains the interference pigment of the present invention.

An ink of the present invention contains the interference pigment of the present invention.

A resin composition of the present invention contains the interference pigment of the present invention.

Effect of the Invention

The present invention provides an interference pigment that develops vivid interference colors on light-colored bases; and a cosmetic, a paint, an ink, and a resin composition including the interference pigment.

DESCRIPTION OF THE INVENTION

Figure 1:
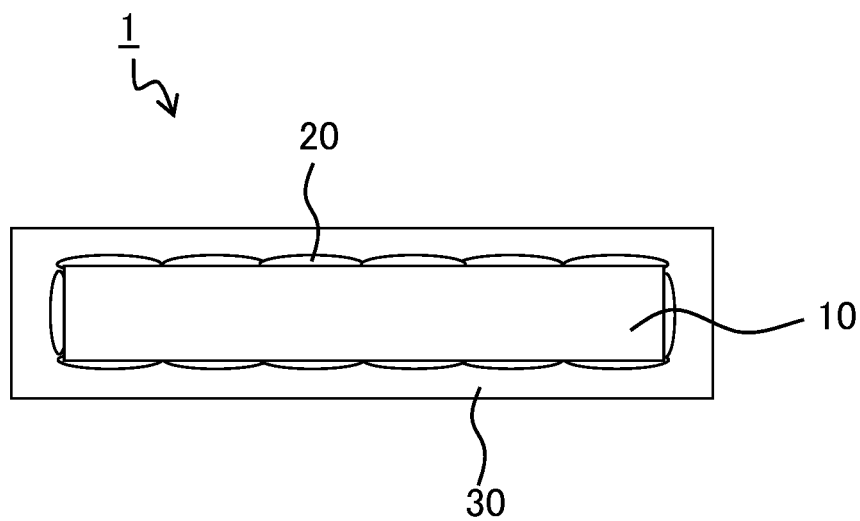
FIG. 1 is a schematic cross-sectional view showing an exemplary interference pigment of the present invention.

In one embodiment, the present invention relates to an interference pigment in which a transparent metal layer coats a flaky inorganic substrate (hereinafter, also referred to as an "inorganic substrate"), and a metal oxide layer coats the transparent metal layer. The present invention is based on the finding that coating the inorganic substrate with the transparent metal layer and the metal oxide layer in this order allows the interference pigment to develop vivid interference colors even on light-colored bases.

Details of the mechanism of the interference pigment of the present invention that can develop vivid interference colors even on light-colored bases have not been clarified, but the following is presumed. Since the inorganic substrate is coated with layers made from different materials such as the metal layer and the metal oxide layer, light interference occurs, upon incidence of visible light into the interference pigment, due to the transmission of light through the metal layer, the metal oxide layer and the inorganic substrate, and the reflection of the light inside the interference pigment (e.g., at an interface between layers in contact with each other). In the conventional interference pigments, light reflected at the base cancels interference colors developed by the interference of the light (especially when the base color is white), and interference colors are hardly recognized. Meanwhile, in the interference pigment of the present invention, the metal layer arranged between the metal oxide layer and the inorganic substrate (arranged on the inorganic substrate side seen from the metal oxide layer) functions as a light absorbing layer to moderately absorb light, thereby absorbing part of the light reflected at the base and reducing the force of cancelling interference colors. As a result, interference colors exhibited by the interference pigment become vivider, and thus the interference pigment can develop more vivid interference colors even on light-colored bases. The mechanism of the present invention, however, is not limited to the above-described mechanism.

Since the interference pigment of the present invention includes layers made from different materials such as the transparent metal layer and the metal oxide layer, it can develop colors such as pale pink and pale purple that can hardly be obtained by conventional interference pigments composed of, e.g., a transparent flaky substrate and a metal oxide layer that coats the flaky substrate. When the interference pigment of the present invention is applied to light-colored bases or used in the form of powder such as powder cosmetics (e.g., eyeshadows, powder foundations), it can develop vivid interference colors.

In non-limiting preferable embodiments, the present invention relates to an interference pigment including: a flaky inorganic substrate; a metal oxide layer (hereinafter, also referred to as a "second metal oxide layer") that coats the inorganic substrate; a transparent metal layer that coats the second metal oxide layer; and a metal oxide layer (hereinafter, also referred to as a "first metal oxide layer") that coats the transparent metal layer. The interference pigment of the present embodiment can cause even stronger interference, thereby developing more vivid interference colors.

The "interference pigment" in the present specification refers to a pigment that exhibits interference colors, preferably a pigment that causes light interference upon incidence of visible light beams to the interference pigment while reflecting part of incident light inside the pigment and passing the remaining incident light. It can also be developed that the "interference pigment" in the present specification refers to, e.g., a pigment including at least one reflection surface that can reflect part of incident light and that can pass the other incident lights. The reflection surface may be, e.g., an interface between layers that are formed from materials having different refractive indices. Examples of the interface include an interface between the inorganic substrate and a layer adjacent to the inorganic substrate, an interface between layers adjacent to each other (e.g., an interface between the metal oxide layer and the transparent metal layer adjacent to the metal oxide layer), etc.

The "interference colors" in the present specification are colors to be developed upon incidence of visible light beams to the interference pigment, by mutually strengthened lights reflected at, e.g., an interface between the transparent metal layer and the metal oxide layer adjacent to the metal layer, an interface between the inorganic substrate and a layer adjacent to the inorganic substrate, etc. The interference colors to be exhibited by the interference pigment of the present invention may vary depending on the base color of a cosmetic, a paint, a resin composition, etc., to be blended with the interference pigment, and/or the observation angle of reflected light reflected at the interference pigment. Examples of the interference colors include colors of reflected light reflected at the surface and/or the interface of the interference pigment, or colors of transmitted light transmitted through the interference pigment. These colors may vary depending on the base color. The "vivid interference colors" in the present specification mean that interference of light reflected inside the interference pigment, etc., is strong, or interference colors developed by light interference are strong. The "pale interference colors" in the present specification indicate that the luminosity of colors developed by interference is high, preferably the value is high but the Chroma is low. The pale interference colors may be, e.g., pastel colors, and examples of the pastel colors include mixed colors (e.g., pale yellow, pale blue, pale pink, and pale purple) obtained by mixing pure color (e.g., red, blue, and purple) with white.

The "base color" in the present specification refers to the color of an object on which a cosmetic, a paint, an ink, or a resin composition blended with the interference pigment of the present invention is applied, or the color of a base material constituting a cosmetic, a paint, an ink, or a resin composition to be blended with the interference pigment of the present invention.

The "transparent metal layer" in the present specification refers to a layer containing one kind metal or an alloy through which a layer other than the transparent metal layer can be seen. The layer other than the transparent metal layer is, e.g., a layer that is located on the inner side (the inorganic substrate side) of the transparent metal layer and that is in contact with the transparent metal layer, such as the inorganic substrate or the metal oxide layer. The transparent metal layer may be provided continuously or discontinuously. The discontinuous case is, e.g., a case in which another transparent metal layer is partially formed on the surface of an object coated with the transparent metal layer. For example, the transparent metal layer may be partially formed between the inorganic substrate and the metal oxide layer. The continuous case is, e.g., another transparent metal layer is formed on the entire surface of an object coated with the transparent metal layer.

The average thickness of the transparent metal layer is, e.g., 5 nm or less, preferably less than 5 nm, more preferably 3 nm or less, further preferably 1 nm or less, still further preferably 0.1 nm or less, still further preferably 0.09 nm or less, still further preferably 0.08 nm or less, and still further preferably 0.07 nm or less, for the reason that within the above range metallic luster is hardly recognized and the transparent metal layer can moderately absorb reflected light reflected at the base. The lower limit of the average thickness of the transparent metal layer is, e.g., 0.01 nm or more, preferably 0.03 nm or more, from the viewpoint of moderately absorbing reflected light reflected at the base. The average thickness of the transparent metal layer can be calculated by the method described in examples.

The thickness of the transparent metal layer can be calculated from, e.g., the amount and the specific gravity of the metal contained in the transparent metal layer and the surface area of the object coated with the transparent metal layer. Therefore, the thickness of the transparent metal layer calculated from the amount and the specific gravity of the metal contained in the transparent metal layer and the surface area of the object coated with the transparent metal layer is, e.g., 5 nm or less, preferably less than 5 nm, more preferably 3 nm or less, further preferably 1 nm or less, still further preferably 0.1 nm or less, still further preferably 0.09 nm or less, still further preferably 0.08 nm or less, and still further preferably 0.07 nm or less. The lower limit of the average thickness of the transparent metal layer is, e.g., 0.01 nm or more, preferably 0.03 nm or more, from the viewpoint of moderately absorbing reflected light reflected at the base. The "surface area of the object coated with the transparent metal layer" refers to a surface area of a plane on which the transparent metal layer is formed in the object coated with the transparent metal layer. For example, when the transparent metal layer is formed on the surface of the inorganic substrate, it refers to the surface area of the inorganic substrate. When the transparent metal layer is formed on the surface of the metal oxide layer that coats the inorganic substrate, it refers to the surface area of the entire inorganic substrate coated with the metal oxide layer. The amount of the metal contained in the transparent metal layer can be determined using, e.g., the content of the metal. The amount and the content of the metal in the transparent metal layer and the surface area can be calculated by the methods described in examples.

In the interference pigment of the present invention, the metal content in the transparent metal layer is, e.g., 0.1 mass % or less, and preferably 0.08 mass % or less, for the purpose of preventing the development of colors other than interference colors by light absorption of the metal layer. The lower limit of the metal content in the transparent metal layer is not particularly limited as long as at least part of the surface of at least an object to be coated (e.g., inorganic substrate) is coated with the transparent metal layer; however the lower limit may be, e.g., 0.01 mass % or more, preferably 0.03 mass % or more. The "metal content in the transparent metal layer" in the present specification refers to a mass percentage (mass %) of the metal contained in the transparent metal layer with respect to the total weight of the transparent metal layer and the object coated with the transparent metal layer (e.g., inorganic substrate).

The "metal oxide layer" in the present specification refers to a layer containing metal oxide. Examples of the metal oxide include titanium oxide, ferric oxide, iron hydroxide, and mixtures of these.

The average particle diameter of the interference pigment of the present invention is, e.g., 1 µm to 500 µm, from the viewpoint of adequately preventing crush of the interference pigment in the process of blending the interference pigment with a paint or resin composition. The average particle diameter of the interference pigment is preferably 5 µm or more, more preferably 10 µm or more, further preferably 50 µm or more, still further preferably 75 µm or more, and still further preferably 80 µm or more, from the viewpoint of preventing the crush of the interference pigment. The average particle diameter of the interference pigment is preferably 250 µm or less, more preferably 200 µm or less, further preferably 100 µm or less, and still further preferably 90 µm or less from the same viewpoint. The average particle diameter of the interference pigment can be calculated by the method described in examples.

The average thickness of the interference pigment of the present invention is, e.g., 0.1 µm to 10 µm, from the viewpoint of adequately preventing the crush of the interference pigment in the process of blending the interference pigment with a paint or resin composition. The average thickness of the interference pigment is preferably 0.2 µm or more, more preferably 0.3 µm or more, further preferably 0.5 µm or more, still further preferably 0.8 µm or more, and still further preferably 1 µm or more, for the purpose of preventing the crush and defects of the coating film. The average thickness of the interference pigment is preferably 7 µm or less, more preferably 5 µm or less, further preferably 3 µm or less, still further preferably 2.5 µm or less, and still further preferably 2 µm or less, from the same reason. The average thickness of the interference pigment can be calculated by the method described in examples.

In the interference pigment of the present invention, a color difference $\Delta E$ with respect to a blank measured according to the CIE 1976 (L*a*b*) color system preferably exceeds 2, and, for the purpose of obtaining interference pigments exhibiting even paler interference colors, the $\Delta E$ is more preferably 4 or more, further preferably 5 or more, still further preferably 10 or more, still further preferably 11 or more, still further preferably 12 or more, and still further preferably 13 or more. The upper limit of the $\Delta E$ is not limited particularly, but for example, the $\Delta E$ is 20 or less, preferably 18 or less. The $\Delta E$ can be calculated by the method described in examples.

The reflectance for light having a wavelength of 480 nm in the interference pigment of the present invention is, e.g., 50% or more and 90% or less for the reason that the transparent metal layer can moderately absorb light, and preferably 60% or more and 75% or less from the same reason.

The reflectance for light having a wavelength of 580 nm in the interference pigment of the present invention is, e.g., 40% or more and 80% or less for the reason that the transparent metal layer can moderately absorb light, and preferably 50% or more and 70% or less from the same reason.

The reflectance for light having a wavelength of 680 nm in the interference pigment of the present invention is, e.g., 50% or more and 90% or less for the reason that the transparent metal layer can moderately absorb light, and preferably 60% or more and 80% or less, and more preferably 60% or more and 75.5% or less from the same reason.

The transmittance for light having a wavelength of 480 nm in the interference pigment of the present invention is, e.g., 40% or more and 90% or less for the reason that the base color is not hidden when the interference pigment is applied (the base color can be advantageously used), and preferably 50% or more and 90% or less from the same reason.

The transmittance for light having a wavelength of 580 nm in the interference pigment of the present invention is, e.g., 40% or more and 90% or less, preferably 50% or more and 90% or less, for the reason that the base color is not hidden when the interference pigment is applied (the base color can be advantageously used).

The transmittance for light having a wavelength of 680 nm in the interference pigment of the present invention is, e.g., 40% or more and 90% or less, preferably 50% or more and 90% or less, for the reason that the base color is not hidden when the interference pigment is applied (the base color can be advantageously used).

The reflectance and the transmittance of light in the interference pigment can be calculated by the methods described in examples.

The interference pigment of the present invention may include a plurality of layers of at least one of the transparent metal layer and the metal oxide layer, for the purpose of developing vivider interference colors. Specifically, the interference pigment of the present invention may include one metal oxide layer and a plurality of transparent metal layers, or one transparent metal layer and a plurality of metal oxide layers, or a plurality of metal oxide layers and a plurality of transparent metal layres. The term "a plurality of layers (films)" in the present specification indicates 2, 3, 4, 5, or 6 or more layers (films). When the interference pigment includes a plurality of layers of at least one of the transparent metal layer and the metal oxide layer, the transparent metal layer and the metal oxide layer may be formed alternately, or a plurality of the transparent metal layers may be in contact with each other, or a plurality of the metal oxide layers may be in contact with each other. It is particularly preferred that the interference pigment include a laminated layer that includes transparent metal layers and metal oxide layers that are laminated alternately, and the laminated layer coat the first metal oxide layer (the metal oxide layer that coats the transparent metal layer), for the purpose of enhancing the interference.

In the interference pigment of the present invention, it is preferred that the transparent metal layer be coated with the metal oxide layer, for the purpose of developing pale interference colors mixed with white color of the base.

Embodiment 1

In Embodiment 1, an exemplary interference pigment of the present invention will be described by referring to a configuration in which the interference pigment includes one transparent metal layer and one metal oxide layer.

FIG. 1 is a schematic cross-sectional view showing an exemplary interference pigment of Embodiment 1. As illustrated in FIG. 1, an interference pigment 1 includes: a flaky transparent inorganic substrate 10; a transparent metal layer 20 that coats the surface of the inorganic substrate 10; and a metal oxide layer 30 that coats the inorganic substrate 10 from the outer side of the transparent metal layer 20. In other words, the interference pigment of Embodiment 1 includes the transparent metal layer 20 arranged on the inorganic substrate 10 side seen from the metal oxide layer 30. The transparent metal layer 20 is interposed between the inorganic substrate 10 and the metal oxide layer 30 so as to be adjacent to the inorganic substrate 10 and the metal oxide layer 30.

As illustrated in FIG. 1, the entire surface of the inorganic substrate 10 is coated with the transparent metal layer 20. The metal oxide layer 30 is formed to coat the entire surface of the transparent metal layer 20.

[Inorganic Substrate]

It is preferred that the inorganic substrate is transparent for light-colored base, for the purpose of providing an interference pigment that can develop paler interference colors when mixed with the base color. Examples of the transparent inorganic substrate include substrates that contain at least one selected from the group consisting of glass, mica, silica, and alumina, preferably substrates substantially made from at least one material selected from the group consisting of glass, mica, silica, and alumina. The "substrates substantially made from at least one material selected from the group consisting of glass, mica, silica, and alumina (hereinafter, also referred to as "substrate material")" in the present specification means that the substrate is formed from the substrate material only, except for impurities inevitably contained in the raw material of the inorganic substrate and/or impurities inevitably mixed in the production process of the inorganic substrate. More specifically, the content of the substrate material in the inorganic substrate is, e.g., 99 atom % or more, preferably 99.5 atom % or more, and more preferably substantially 100 atom %.

Of these, glass is preferred as the material of the inorganic substrate, for the purpose of obtaining high transparency. The composition of glass is not particularly limited as long as a known glass composition from which flaky glass can be formed is used. Favorable examples of glass compositions include glass compositions C and E used for glass fibers, for the purpose of easy formation of the flaky glass substrate. Japanese Industrial Standard (JIS) R3410 specifies each of C glass and E glass Generally, C glass refers to glass having an alkaline oxide ($Na_2O+K_2O$) content of about 5 to 20% and is also called alkali-containing glass E glass refers to glass compositions having an alkali ($Na_2O$, $K_2O$) content of 2.0% or less and is also called non-alkali glass.

For the inorganic substrate, a flaky glass substrate produced by blowing is preferred, for the purpose of easily obtaining an inorganic substrate with a smooth surface. In blowing, a raw cullet is melted. The molten glass is discharged continuously from a circular slit while gas (e.g., air) is blown into the glass through blow nozzles formed in the interior of the circular slit. As a result, the molten glass is stretched and expanded to have a balloon shape. The balloon shaped glass is pulverized to obtain a flaky glass substrate.

Examples of marketed flaky glass substrates include MICROGLAS (registered trademark) GLASFLAKE (registered trademark) series (RCF-160, REF-160, RCF-015, REF-015) manufactured by Nippon Sheet Glass Co., Ltd.

The average particle diameter and the average thickness of the inorganic substrate can be determined appropriately depending on the intended use of the interference pigment. Generally, the inorganic substrate has an average particle diameter of preferably 1 μm to 500 μm. Within the above-described range of the average particle diameter, it is possible to adequately prevent the crush of the interference pigment in the process of blending the interference pigment with a paint or resin composition. Further, within the above-described range of the average particle diameter, when the interference pigment is blended with a paint or resin, the principle plane of the interference pigment in the coating film, resin composition, etc., to be obtained will be oriented substantially in a constant direction. Thus, scattering of light reflected at the respective interference pigment can be avoided. The adequate prevention of the crush of the interference pigment, especially when the inorganic substrate contains glass, can prevent alkaline components contained in the glass from diffusing into the paint or resin composition. The average particle diameter of the inorganic substrate is more preferably 5 μm to 250 μm, further preferably 10 μm to 150 μm, for the purpose of preventing the crush.

The "average particle diameter of the inorganic substrate" in the present specification refers to a particle diameter (D50) that corresponds to a particle diameter at which the cumulative volume of particles reaches 50% in the particle diameter distribution. The particle diameter distribution is an index showing the sizes (particle diameters) and the percentages of particles contained in a particle group (object to be measured). The average particle diameter can be measured based on the laser diffraction scattering method, and determined by the method described in examples. In the laser diffraction scattering method, the particle diameter distribution is determined by utilizing scattered light at the time of irradiating particles with light.

Generally, it is preferred that the inorganic substrate have an average thickness of 0.1 μm to 10 μm. Within the above-described range of the average thickness, it is possible to adequately prevent the crush of the interference pigment in the process of blending the interference pigment with a paint or resin composition. The adequate prevention of the crush of the interference pigment, especially when the inorganic substrate contains glass, can prevent alkaline components contained in the glass from diffusing into the paint or resin composition. Moreover, within the above-described range of the average thickness, when the interference pigment is blended with a paint or resin, the principle plane of the interference pigment in the coating film, resin composition, etc., to be obtained will be oriented substantially in a constant direction. Thus, scattering of light reflected at the respective interference pigment can be avoided. The average thickness of the inorganic substrate is more preferably 0.2 μm to 7 μm, further preferably 0.3 μm to 5 μm, for the purpose of preventing the crush and defects of the coating films.

The average thickness of the inorganic substrate is determined by measuring the thicknesses of 100 inorganic substrate grains and averaging the thicknesses. The thickness of each inorganic substrate is determined by measuring an optical-path difference between direct light emitted to the inorganic substrate (light not influenced by a phase object) and light passed through the inorganic substrate, with use of an interference microscope. Further, the average thickness of the inorganic substrate in the interference pigment can be measured using a scanning electron microscope (SEM). Specifically, the thickness of the inorganic substrate can be determined by enclosing the interference pigment in a resin, freeze-drying it by liquid nitrogen, fracturing the freeze-dried resin, and measuring the thickness of the inorganic substrate from the fractured cross-sections.

The refractive index of the inorganic substrate is determined depending on the material of the inorganic substrate. When the inorganic substrate is glass, the refractive index is 1.5 to 1.6, for example. The refractive index of the inorganic substrate can be measured in accordance with the Becke's line method, with use of an Abbe refractometer. Specifically, an inorganic substrate placed on a deck glass is impregnated with a refraction liquid by dropping, and a cover glass is placed thereon. A microscope is used to trace Becke's line (bright line along the circumference of the sample). The Becke's line moves toward a medium of higher refractive index when the microscope tube is raised, and moves toward a medium of lower refractive index when the microscope tube is lowered. The refractive index of the refraction liquid is changed successively, and the Becke's line is traced until the Becke's line stops moving. In this manner, the refractive index of the sample (inorganic substrate) is narrowed. After the refraction liquids having a refractive index (above and below) close to that of the sample (inorganic substrate) are found, the refractive indices of the refraction liquids are assayed and read up to 0.001 with the Abbe refractometer, and then they are averaged to obtain the refractive index of the inorganic substrate.

[Transparent Metal Layer]

The transparent metal layer 20 includes one kind metal or a metal alloy, preferably it is substantially formed from one kind metal or a metal alloy. Examples of the metal to be contained in the transparent metal layer include silver, gold, platinum, and palladium. The transparent metal layer 20 preferably includes gold or silver, more preferably it is substantially formed from gold alone, silver alone, gold alloy, or silver alloy, for the purpose of easily obtaining interference pigments exhibiting pale interference colors. The "substantially formed from one kind metal or a metal alloy" in the present specification means that the transparent metal layer 20 is formed from one kind metal or a metal alloy only, except for impurities inevitably contained in the raw material of the transparent metal layer and/or impurities inevitably mixed in the production process of the transparent metal layer. More specifically, the content of the one kind metal or metal alloy in the transparent metal layer is, e.g., 99 atom % or more, preferably 99.5 atom % or more, and more preferably substantially 100 atom %.

Examples of the metal alloy include: binary alloys such as a silver-gold alloy, a silver-platinum alloy, a silver-palladium alloy, a gold-platinum alloy, a gold-palladium alloy, a platinum-palladium alloy; ternary alloys such as a sliver-gold-palladium alloy, a sliver-platinum-palladium alloy, a silver-gold-platinum alloy, a gold-platinum-palladium alloy; and quaternary alloys such as a silver-gold-platinum-palladium alloy.

The metal that can be contained in the transparent metal layer preferably has high light absorptivity.

The refractive index of the metal is generally expressed as a complex refractive index (N), which is defined by a refractive index (n) and an extinction coefficient (k) (in the following formula, i indicates an imaginary unit ($i^2=-1$)). Table 1 below shows the refractive indices (n) and the extinction coefficients (k) of silver, gold, platinum, and palladium.

Complex refractive index (N)=n−ik

TABLE 1

| | Refractive index (n) | Extinction coefficient (k) |
|---|---|---|
| Silver | 0.05 | 2.87 |
| Gold | 0.84 | 1.84 |
| Palladium | 1.68 | 3.67 |
| Platinum | 2.63 | 3.54 |

[Metal Oxide Layer]

The metal oxide layer 30 contains metal oxide, preferably it is substantially formed from metal oxide. The metal oxide is, e.g., at least one selected from the group consisting of titanium oxide, ferric oxide, and iron hydroxide. Titanium oxide is preferred for the reason that it has high refractive index and high chemical stability. The "substantially formed from metal oxide" in the present specification means that the metal oxide layer 30 is formed from metal oxide only, except for impurities inevitably contained in the raw material of the metal oxide layer and/or impurities inevitably mixed in the production process of the metal oxide layer. More specifically, the content of the metal oxide in the metal oxide layer is, e.g., 99 atom % or more, preferably 99.5 atom % or more, and more preferably substantially 100 atom %.

The metal oxide layer 30 and the transparent metal layer 20 contain different kinds of metals.

The average thickness of the metal oxide layer is preferably 20 nm to 350 nm, more preferably 40 nm to 350 nm, further preferably 50 nm to 300 nm, still further preferably 50 nm to 250 nm, still further preferably 80 nm to 200 nm, for the purpose of increasing optical interference. The average thickness of the metal oxide layer can be determined by the method described in examples.

The refractive index of the metal oxide layer can be determined appropriately depending on the kind of the metal oxide contained in the metal oxide layer, desired interference colors, etc., but it is preferably 1.8 to 3.3, more preferably 2.3 to 3.3. The refractive indices of the metal oxides that can be contained in the metal oxide layer are, for example, titanium oxide (rutile crystal phase) (2.71), ferric oxide (3.01), and iron hydroxide (2.33) (the numbers in parentheses are the refractive indices of the respective metal oxides).

The following describes a case of using titanium dioxide or ferric oxide for the metal oxide layer.

<Titanium Dioxide Layer>

Titanium dioxide has three types of crystal forms such as anatase, brookite, and rutile. Of these, titanium dioxide is preferably anatase titanium dioxide or rutile titanium dioxide because they have been produced industrially, and more preferably rutile titanium dioxide. If an interference pigment includes a rutile titanium oxide layer as the metal oxide layer, it is possible to inhibit, when the interference pigment is blended with a resin or paint, the decomposition or discoloration of the resin or paint due to the photocatalytic activity of the metal oxide (rutile titanium oxide) contained in the metal oxide layer. By using the rutile titanium oxide, it is possible to easily form a dense and uniform titanium dioxide layer with high refractive index. Moreover, by using the rutile titanium oxide, it is possible to obtain a titanium dioxide layer that exhibits excellent color developing properties by light interference. Preferably, the metal oxide layer is substantially made from rutile titanium dioxide. The average thickness of the rutile titanium oxide is preferably 20 nm to 350 nm, more preferably 50 nm to 300 nm, further preferably 70 nm to 250 nm, and still further preferably 80 nm to 200 nm.

<Ferric Oxide Layer>

If an interference pigment includes a ferric oxide layer as the metal oxide layer, it is possible to inhibit, when the interference pigment is blended with a resin or paint, the decomposition or discoloration of the resin or paint due to the photocatalytic activity of the metal oxide contained in the metal oxide layer. Moreover, an interference pigment including a ferric oxide layer can exhibit more colors different from the colors to be exhibited by the titanium oxide layer, by light absorption or light reflection of the ferric oxide layer. The average thickness of the ferric oxide layer is preferably 20 nm to 300 nm.

[Production Method of Interference Pigment]

The interference pigment of Embodiment 1 can be obtained by, e.g., a production method including: a step of coating the surface of a flaky transparent inorganic substrate with a transparent metal layer (metal layer coating step); and a step of coating the inorganic substrate coated with the transparent metal layer with a metal oxide layer so as to coat the transparent metal layer (metal oxide layer coating step).

[Metal Layer Coating Step]

In the metal layer coating step, the inorganic substrate is coated with a metal layer containing one kind metal or a metal alloy and calcined. The metal layer can be formed by, e.g., sputtering, chemical-vapor deposition (CVD), or electroless (chemical) plating. Of these methods, electroless plating is preferable because a uniform layer can be formed easily on the flaky transparent inorganic substrate.

As the metal material of a plating solution used in the electroless plating, one of the following compounds can be used. A metal alloy layer can be formed by mixing or the like of these metal materials.

(1) Silver material: silver nitrite
(2) Gold material: sodium gold(I) sulfite, gold(III) chloride [tetrachloro-gold(III) tetrahydrate]
(3) Platinum material: platinum(IV) chloride[hexachloro platinum(IV) hexahydrate], potassium platinum(IV) chloride, sodium platinum(IV) chloride, sodium hexahydroxoplatinum(IV) hydrate, potassium platinum(II) chloride, dinitrodiammine platinum(II), potassium tetranitroplatinum(II), tetraamminedichloro platinum(II)
(4) Palladium material: dinitrodiammine palladium(II) (diamino-palladium nitrite), palladium(II) chloride, sodium palladium(II) chloride, palladium(II) nitrite dihydrate, dichlorotetraammine palladium(II) monohydrate (tetraammine palladium(II) dichloride), dichlorodiammine palladium(II)

In the metal layer coating step, it is preferred that the inorganic substrate be subjected to pretreatment before being coated with the metal layer. The pretreatment is preferably performed with tin because tin facilitates uniform coating of metal such as gold or silver. The pretreatment with tin can be performed in the following manner, for example. First, inorganic substrate is dispersed in water. While stirring, the pH is adjusted to 1.4 to 1.6 with acid to prepare a slurry containing the inorganic substrate. After adding an aqueous solution of tin chloride to the obtained slurry, the pH is adjusted to 1.4 to 1.6 with acid, and the mixture is stirred for a predetermined time and washed with water. The acid may be, e.g., hydrochloric acid, nitric acid, etc.

[Metal Oxide Layer Coating Step]

In the metal oxide layer coating step, the inorganic substrate coated with the transparent metal layer is coated with a metal oxide layer. The metal oxide layer can be formed by a known method, using at least one selected from the group consisting of titanium oxide, ferric oxide, and iron hydroxide. The following describes methods of forming layers, taking a titanium dioxide layer and a ferric oxide layer as examples.

<Titanium Dioxide Layer>

The rutile titanium dioxide layer can be produced by, e.g., causing a neutralization reaction in a solution containing titanium under conditions of a temperature of 55° C. to 85° C. and a pH of 1.3 or less to precipitate rutile titanium dioxide from the solution (e.g., JP 2001-31421 A). In this method, since heating for transforming the crystal form is not basically necessary, a rutile titanium dioxide layer can be formed even on, e.g., inorganic substrates with low heat resistance.

<Ferric Oxide Layer>

The ferric oxide layer can be produced by, e.g., causing a neutralization reaction in a solution containing iron under conditions of a temperature of 50° C. to 80° C. and a pH of 2 to 4 to precipitate ferric oxide from the solution (e.g., JP 2005-187782 A).

Next, the inorganic substrate coated with the metal oxide layer is heated under an atmosphere exceeding 300° C. This heating promotes the crystallization of the metal oxide constituting the coated metal oxide layer. When the metal oxide layer is a titanium oxide layer for example, heating can promote the crystallization into rutile titanium oxide.

The temperature of the atmosphere for heating the inorganic substrate coated with the metal oxide layer is over 300° C., preferably 450° C. or more, and more preferably 600° C. or more, for the purpose of promoting the crystallization of the metal oxide constituting the metal oxide layer. The upper limit of the heating temperature is not particularly limited as long as the inorganic substrate can withstand the temperature, but it is preferably 1000° C. or less. Therefore, the heating temperature is over 300° C., preferably 300° C. to 1000° C., more preferably 400° C. to 1000° C., and further preferably 400° C. to 750° C. The heating time is preferably 1 to 10 hours, more preferably 2 to 6 hours, for the purpose of applying a sufficient amount of heat to the inorganic substrate to promote the crystallization.

In the metal oxide layer coating step, it is preferred that the coating object (the inorganic substrate coated with the metal layer) be subjected to pretreatment before being coated with the metal oxide layer. The pretreatment can be performed in the same manner as in the metal layer coating step described above.

Embodiment 2

In Embodiment 2, another exemplary interference pigment of the present invention will be described by referring to a configuration in which the interference pigment includes one transparent metal layer and two metal oxide layers.

Figure 2:
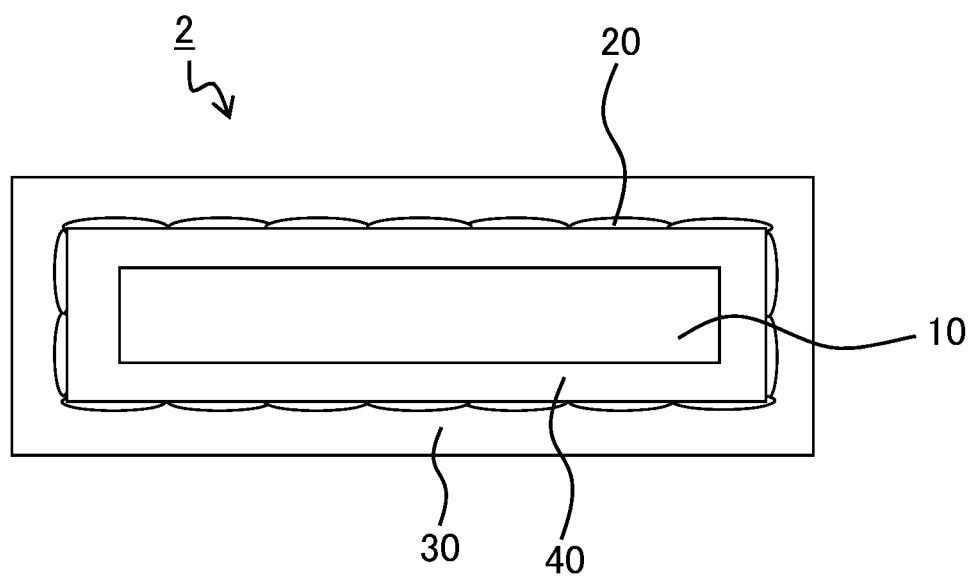
FIG. 2 is a schematic cross-sectional view showing another exemplary interference pigment of the present invention.

FIG. 2 is a schematic cross-sectional view showing an exemplary interference pigment of Embodiment 2. In FIG. 2, the same components as those in Embodiment 1 are denoted with the same reference numerals as in FIG. 1, and the explanation will not repeated.

As illustrated in FIG. 2, an interference pigment 2 includes: a first metal oxide layer 30; a transparent metal layer 20; a second metal oxide layer 40; and a flaky transparent inorganic substrate 10. The second metal oxide layer 40, the transparent metal layer 20, and the first metal oxide layer 30 are laminated on the flaky transparent inorganic substrate 10 in this order to coat the flaky transparent inorganic substrate 10. Specifically, the interference pigment of Embodiment 2 includes the transparent metal layer 20 arranged on the inorganic substrate 10 side seen from the first metal oxide layer 30. The transparent metal layer 20 is arranged between the first metal oxide layer 30 and the second metal oxide layer 40 so as to be adjacent to these layers. The second metal oxide layer 40 is arranged between the inorganic substrate 10 and the transparent metal layer 20 so as to be adjacent to these layers. The outermost layer is the first metal oxide layer 30. By arranging the transparent metal layer under (on the inorganic substrate side) the metal oxide layer and alternately laminating the transparent metal layer and the metal oxide layers, reflection increases due to the refractive index difference, and light interference increases due to the optical distance (optical path difference). Thus, interference pigments that can exhibit even paler color tones can be obtained.

The interference pigment of Embodiment 2 can be produced in the same manner as in the production method of the interference pigment of Embodiment 1, via the metal layer coating step and the metal oxide layer coating step.

The thickness of the first metal oxide layer 30 is, e.g., 20 nm to 350 nm, preferably 50 nm to 300 nm, more preferably 70 nm to 250 nm, further preferably 80 nm to 200 nm, and still further preferably 120 nm to 180 nm. The thickness of the second metal oxide layer 40 is, e.g., 20 nm to 350 nm, preferably 50 nm to 300 nm, more preferably 70 nm to 200 nm, further preferably 80 nm to 150 nm, and still further preferably 80 nm to 100 nm.

In Embodiment 2, the interference pigment includes one transparent metal layer and a plurality (two layers) of metal oxide layers; however, the present invention is not limited to this configuration. Both of the metal oxide layer and the transparent metal layer may be formed in a plural number. When the interference pigment includes a plurality of layers of the metal oxide layer and/or the transparent metal layer, the number is not limited to 2, and may be 3, 4, or 5 or more.

Embodiments 1 and 2 (FIGS. 1 and 2) exemplify the interference pigments including the flaky transparent inorganic substrate, the transparent metal layer, and the metal oxide layer; however, the configurations of the interference pigments of Embodiments 1 and 2 are not limited thereto. For example, the interference pigments of Embodiments 1 and 2 may include layers formed from other components, in addition to the flaky transparent inorganic substrate, the transparent metal layer, and the metal oxide layer. The layers formed from other components may be formed, e.g., between the flaky transparent inorganic substrate and the transparent metal layer, between the transparent metal layer and the first metal oxide layer, between the flaky transparent inorganic substrate and the second metal oxide layer, etc.

The layers formed from other components may be, e.g., polyvalent metal compound layers. Examples of the polyvalent metal compound layers include layers containing a hydroxide or hydrated oxide of at least one element selected from the group consisting of lanthanum, cerium, neodymium, and aluminum. Such polyvalent metal compound layers can impart high weather resistance to interference pigments. For example, when the interference pigment of the present invention is used in automobiles or motorcycles used outdoors, the polyvalent metal compound layers can inhibit the photocatalytic activity of metal oxide (e.g., titanium and iron oxide) in the metal oxide layer due to exposure to ultraviolet light, and thus inhibit the degradation or discoloration of the coating layer due to metal oxide. For the purpose of absorbing ultraviolet light and improving weather resistance of the interference pigment, it is preferred that the polyvalent metal compound layer coat the metal oxide layer. Moreover, for the purpose of improving weather resistance and water resistance secondary adhesion (adhesion after weathering test) of the interference pigment, it is more preferred that the interference pigment include a surface treatment layer as the outermost layer that is prepared using an organic compound containing an oxazoline ring and/or a silane coupling agent.

The following describes the layers formed from other components, taking layers of a hydroxide or hydrated oxide of cerium, lanthanum, or aluminum as examples.

<Hydroxide Layer or Hydrated Oxide Layer of Cerium>

A hydroxide layer or hydrated oxide layer of cerium (hereinafter, also referred to as a "cerium layer") can be formed by reacting a water-soluble cerium compound with acid or alkali to precipitate a hydroxide or hydrated oxide of cerium on the surface of a coating object. Examples of the water-soluble cerium compound include acidic cerium compounds and alkaline cerium compounds. In the case of using the acidic cerium compound as the water-soluble cerium compound, a cerium layer can be formed by reacting an acidic cerium compound with alkali (e.g., alkali metal hydroxide) to precipitate a hydroxide or hydrated oxide of cerium on the surface of the coating object. Meanwhile, in the case of using the alkaline cerium compound as the water-soluble cerium compound, a cerium layer can be formed by reacting an alkaline cerium compound with acid (e.g., sulfuric acid) to precipitate a hydroxide or hydrated oxide of cerium on the surface of the coating object. Examples of the acidic cerium compound include cerium mineral acid salts such as cerium sulfate, cerium chloride, and cerium nitrate. Examples of the alkaline cerium compound include alkaline cerium salts such as ammonium cerium sulfate and ammonium cerium nitrate. The water-soluble cerium compound is preferably cerium nitrate, and the cerium layer is preferably formed by using cerium nitrate and a sodium hydroxide solution. In the formation of the cerium layer, the amount of the cerium compound to be added to the solution (aqueous slurry) for the above-described precipitation is preferably in a range from about 0.01 mass % to about 1.0 mass %, more preferably in a range from about 0.02 mass % to about 0.5 mass % in terms of cerium, with respect to the amount (coating amount) of metal oxide (e.g., titanium dioxide and iron oxide) contained in the metal oxide layer that coats the inorganic substrate. The amount of acid or alkali to be used can be determined appropriately depending on the amount of the cerium compound. For example, acid or alkali is added to the slurry in an amount sufficient to react with the cerium compound to precipitate a hydroxide or hydrated oxide of cerium on the surface of the coating object.

<Hydroxide Layer or Hydrated Oxide Layer of Lanthanum>

A hydroxide layer or hydrated oxide layer of lanthanum (hereinafter, also referred to as a "lanthanum layer") can be formed by reacting a water-soluble lanthanum compound with acid or alkali to precipitate a hydroxide or hydrated oxide of lanthanum on the surface of a coating object. Examples of the water-soluble lanthanum compound include mineral acid salts such as lanthanum sulfate, lanthanum chloride, lanthanum nitrate, lanthanum acetate, and lanthanum carbonate. In the case of using these lanthanum compounds, a lanthanum layer can be formed by reacting these lanthanum compounds with alkali (e.g., alkali metal hydroxide) to precipitate a hydroxide or hydrated oxide of lanthanum on the surface of the coating object. The water-soluble lanthanum compound is preferably lanthanum nitrate. Preferably, the lanthanum layer is formed by using lanthanum nitrate and a sodium hydroxide solution. The amount of the lanthanum compound to be added to the solution (aqueous slurry) for the above-described precipitation is preferably in a range from about 0.01 mass % to about 1.0 mass %, more preferably in a range from about 0.02 mass % to about 0.5 mass % in terms of lanthanum, with respect to the amount (coating amount) of metal oxide (e.g., titanium dioxide and iron oxide) contained in the metal oxide layer that coats the inorganic substrate. The amount of acid or alkali to be used can be determined appropriately depending on the amount of the lanthanum compound. For example, acid or alkali is added to the slurry in an amount sufficient to react with the lanthanum compound to precipitate a hydroxide or hydrated oxide of lanthanum on the surface of the coating object.

<Hydroxide Layer or Hydrated Oxide Layer of Aluminum>

A hydroxide layer or hydrated oxide layer of aluminum (hereinafter, also referred to as an "aluminum layer") can be formed by reacting an acidic or alkaline aluminum compound with appropriate acid or alkali to precipitate a hydroxide or hydrated oxide of aluminum on the surface of a coating object. Examples of the acidic aluminum compound include mineral acid aluminum salts such as aluminum chloride, aluminum sulfate, and aluminum nitrate. Examples of the alkaline aluminum compound include alkali metal aluminates such as sodium aluminate. The amount of the aluminum compound to be added to the solution (aqueous slurry) for the above-described precipitation is preferably in a range from about 2 mass % to about 4 mass %, more preferably in a range from about 2.5 mass % to about 3.5 mass % in terms of aluminum, with respect to the amount (coating amount) of metal oxide (e.g., titanium dioxide and iron oxide) contained in the metal oxide layer that coats the inorganic substrate. The acid or alkali to be used for reaction may be added simultaneously or subsequent to the addition of the aluminum compound to the solution. The amount of acid or alkali to be used can be determined appropriately depending on the amount of the aluminum compound. For example, acid or alkali is added to the slurry in an amount sufficient to cause a hydroxide or hydrated oxide of aluminum to precipitate on the surface of the coating object.

Embodiment 3

In Embodiment 3, an exemplary paint of the present invention will be described.

The paint of the present invention contains the interference pigment of the present invention, preferably contains the interference pigment of the present invention, a resin, and a solvent. The paint of the present invention may further contain a curing agent as needed. The application areas of the paint of the present invention include the exterior of automobiles, motorcycles and bicycles, buildings, tiles, furniture, utensils, containers, office supplies, sporting goods, and the like.

The interference pigment contained in the paint preferably has an average particle diameter of, e.g., 1 μm to 50 μm and an average thickness of, e.g., 0.1 μm to 3 μm. Filtration is performed to remove foreign substances when paint is used cyclically in the painting process of car panels, etc. Within the above-described range of the average particle diameter, an increase in pressure loss due to the filtration or deterioration of the coating quality according to the reduction in the content of the interference pigment in the paint can be avoided. Moreover, within the above-described range of the average particle diameter, the interference pigment can be prevented from sticking out from the surface of the coating layer formed while the orientation of the interference pigment in the coating layer is improved, making the finished quality of the coating layer favorable.

Examples of the resin include thermosetting resins, such as an acrylic resin, a polyester resin, an epoxy resin, a phenol resin, a urea resin, a fluorocarbon resin, a polyester-urethane curable resin, an epoxy-polyester curable resin, an acrylic-polyester based resin, an acrylic-urethane curable resin, an acrylic-melamine curable resin and a polyester-melamine curable resin, and thermoplastic resins, such as a polyethylene resin, a polypropylene resin, a petroleum resin, a thermoplastic polyester resin and a thermoplastic fluorocarbon resin.

Examples of the solvent include: aliphatic hydrocarbons (for example, hexane, heptane, octane, etc.); esters (for example, ethyl acetate, n-butyl acetate, isobutyl acetate, n-butyl acetate, etc.); ketones (for example, acetone, methyl ethyl ketone, methyl isobutyl ketone, etc.); ethers (for example, diethyl ether, dioxane, tetrahydrofuran, etc.); cellosolves (for example, methyl cellosolve (ethylene glycol monomethyl ether), ethyl cellosolve, propyl cellosolve, butyl cellosolve, phenyl cellosolve, benzyl cellosolve, etc.); and carbitols (for example, diethylene glycol monomethyl ether, carbitol (diethylene glycol monoethyl ether), diethylene glycol monopropyl ether, etc.). They may be used in a combination of two or more kinds.

Examples of the curing agent include polyisocyanate, amine, polyamide, polybasic acid, acid anhydride, polysulfide, trifluoroboric acid, acid dihydrazide and imidazole.

The content of each component in the paint is not limited in the present invention, and it can be determined appropriately based on that in conventionally known paints.

The content of the interference pigment in the paint is preferably 0.1 to 30 mass %, more preferably 1 to 20 mass % in a dry-cured coating layer.

The content of the resin in the paint is preferably 20 to 80 mass %, more preferably 30 to 60 mass % in a dry-cured coating layer, for the purpose of improving the efficiency of coating adhesion.

The content of the solvent in the paint is not particularly limited and it may be set in accordance with the application method of the paint. For example, when the application method is spray coating, it is preferable to determine the content of the solvent such that the viscosity of the paint at 20° C. becomes 10 to 30 Pa·s.

The paint of the present embodiment may further contain a pigment other than the interference pigment of the present invention, a surfactant, a lubricant, an antifoaming agent, and/or a leveling agent, etc.

Embodiment 4

In Embodiment 4, an exemplary resin composition of the present invention will be described.

The resin composition of the present invention contains the interference pigment of the present invention, preferably contains the interference pigment of the present invention and a base resin. The resin composition of the present invention may further contain a curing agent as needed. Examples of molded products that can be molded using the resin composition of the present embodiment include cosmetic containers, food containers, wall materials, floor materials, cases for household electric appliances, accessories, stationeries, toys, bathtubs, bath equipment, shoes, sporting goods, toilet goods and the like.

The interference pigment contained in the resin composition preferably has an average particle diameter of, e.g., 30 μm to 600 μm and an average thickness of, e.g., 3 μm to 10 μm. The inorganic substrate constituting the interference pigment preferably has an average particle diameter of, e.g., 20 μm to 500 μm and an average thickness of, e.g., 0.5 μm to 10 μm, for the purpose of enhancing glittering on the surfaces of molded products molded using the resin composition.

The inorganic substrate constituting the interference pigment is preferably glass, because glass does not have high cleavage as possessed by mica and can maintain the same particle diameter even after the injection molding.

Examples of the base resin include thermosetting resins, such as an acrylic resin, a polyester resin, an epoxy resin, a phenol resin, a urea resin, a fluorocarbon resin, a polyester-urethane curable resin, an epoxy-polyester curable resin, an acrylic-polyester based resin, an acrylic-urethane curable resin, an acrylic-melamine curable resin and a polyester-melamine curable resin, and thermoplastic resins, such as a polyethylene resin, a polypropylene resin, a petroleum resin, a thermoplastic polyester resin and a thermoplastic fluorocarbon resin. As the base resin, a thermoplastic resin is preferred because injection molding can be carried out and molded products having a complex shape can be molded.

Examples of the curing agent include polyisocyanate, amine, polyamide, polybasic acid, acid anhydride, polysulfide, trifluoroboric acid, acid dihydrazide, imidazole, etc.

The content of each component in the resin composition is not limited in the present invention, and it can be determined appropriately based on that in conventionally known resin compositions. The content of the interference pigment in the resin composition is preferably 0.01 to 10 mass %, more preferably 0.5 to 5 mass %, for the purpose of increasing designing properties of molded products to be molded using the resin composition.

The resin composition of the present invention may further contain a pigment other than the interference pigment of the present invention, a surfactant, a lubricant, an antifoaming agent, and/or a leveling agent, etc.

Embodiment 5

In Embodiment 5, an exemplary ink of the present invention will be described.

The ink of the present invention contains the interference pigment of the present invention, preferably contains the interference pigment of the present invention and a vehicle. The ink of the present invention can be used as ink for writing instruments such as a variety of ballpoint pens and felt pens and printing ink such as gravure ink and offset ink.

The interference pigment contained in the ink for writing instruments preferably has an average particle diameter of 10 μm to 120 μm and an average thickness of 0.1 μm to 2 μm, for the purpose of further smoothing a handwriting surface.

The interference pigment contained in the printing ink preferably has an average particle diameter of 10 μm to 50 μm and an average thickness of 0.1 μm to 2 μm. This is because plate fogging, contamination of an impression cylinder and plate clogging become less likely to occur, so that the printing suitability becomes favorable. The "plate fogging" in the present specification refers to a phenomenon in which a doctor blade cannot sufficiently scrape off ink on the plate at the time of printing and the ink is transferred to a print object, causing scumming of printed matters.

Examples of the vehicle for the ink for writing instruments include a mixture obtained by mixing at least one selected from the group consisting of an acrylic resin, a styrene-acrylic copolymer, polyvinyl alcohol, polyacrylate, an acryl-vinyl acetate copolymer, a microbe polysaccharide such as xanthan gum and a water-soluble vegetable polysaccharide such as guar gum with a solvent. Examples of the solvent include water, alcohol, hydrocarbon, ester, etc.

Examples of the vehicle for the gravure ink include at least one selected from the group consisting of gum rosin, wood rosin, talloil rosin, lime rosin, rosin ester, a maleate resin, a polyamide resin, a vinyl resin, nitrocellulose, cellulose acetate, ethyl cellulose, chlorinated rubber, cyclized rubber, an ethylene-vinyl acetate copolymer resin, an urethane resin, a polyester resin, an alkyd resin, gilsonite, dammar and shellac, a water-soluble resin obtained by imparting water solubility to one selected from the resins in the above group and a mixture obtained by mixing an oil-in-water (O/W) type resin with a solvent. Examples of the solvent include hydrocarbon, alcohol, ether, ester, water, etc.

Examples of the vehicle for the offset ink include a mixture obtained by mixing a resin such as a rosin-modified phenolic resin, a petroleum resin or an alkyd resin with a solvent. Example of the solvent include plant oils such as linseed oil, tung oil and soybean oil, n-paraffin, isoparaffin, aromatic, naphthene, α-olefin, water, etc.

Each of the above-described vehicles may further contain a dye, a pigment other than the interference pigment of the present invention, a surfactant, a lubricant, an antifoaming agent, and/or a leveling agent, etc.

The content of each component in the ink may be determined appropriately depending on the application purpose of the ink. The content is not limited in the present invention and it may be similar to that in conventionally known inks.

Embodiment 6

In Embodiment 6, an exemplary cosmetic of the present invention will be described.

The cosmetic of the present invention contains the interference pigment of the present invention, and may contain a medium as needed. Examples of the cosmetic include, but not are not limited to, nail cosmetics, facial cosmetics, and makeup cosmetics. Examples of the nail cosmetics include nail enamel, nail colors and nail coatings. Examples of makeup cosmetics include: eye and eyebrow cosmetics such as eye shadows, eyeliners, mascara and eyebrow powders; pencil makeup cosmetics such as eyeliner pencils and lip liner pencils; foundations; blushes; face colors; lipsticks; lip glosses; and makeup cosmetics of a sedimentation type that are kept in a state where a lame agent is sediment in water or a solvent but are moderately shaken to be used.

The content of the interference pigment of the present invention in the cosmetic can be determined appropriately depending on the type of the cosmetic. In the case of nail cosmetics, the content of the interference pigment of the present invention is preferably 0.1 to 50 mass %, more preferably 3 to 40 mass % based on 100 mass % of the total mass of the cosmetic, for the purpose of obtaining high brightness and favorable applicability.

In the case of solid powder cosmetics, the content of the interference pigment of the present invention is preferably 5 to 80 mass %, more preferably 10 to 60 mass % based on 100 mass % of the total mass of the cosmetic, for the purpose of obtaining high brightness and favorable feeling in use. Examples of the solid powder cosmetics include cosmetics obtained by drying a powder after dry filling the powder using a press or the like or wet filling the powder using a volatile solvent, specific examples of which include eye shadows.

In the case of powder cosmetics, they are to be mixed with sebum present on the skin when used. Therefore, the content of the interference pigment of the present invention is preferably 70 to 100 mass % based on 100 mass % of the total mass of the cosmetic. Examples of powder cosmetics include loose powders.

In the case of oily solid cosmetics, the content of the interference pigment of the present invention is preferably 1 to 60 mass %, more preferably 3 to 50 mass % based on 100 mass % of the total mass of the cosmetic, for the purpose of moderately ensuring the effect of the interference pigment of the present invention as a lamé agent and favorable formability. In the case of oily solid cosmetics, the interference pigment of the present invention preferably has an average particle diameter of 10 µm to 250 µm and an average thickness of 0.3 µm to 3 µm. Examples of oily solid cosmetics include lip glosses, lipsticks, and oil eye shadows.

In the case of emulsion makeup cosmetics, the content of the interference pigment of the present invention is preferably 1 to 50 mass %, more preferably 3 to 40 mass % based on 100 mass % of the total mass of the cosmetic, for the purpose of moderately ensuring the effect of the interference pigment of the present invention as a lame agent and high emulsion stability. Examples of the emulsion makeup cosmetics include makeup cosmetics obtained by emulsifying a water phase and an oil phase with an activator.

In the case of aqueous makeup cosmetics, the content of the interference pigment of the present invention is preferably 0.1 to 60 mass %, more preferably 1 to 40 mass % based on 100 mass % of the total mass of the cosmetic, for the purpose of moderately ensuring the effect of the interference pigment of the present invention as a lame agent and favorable feeling in use. Examples of the aqueous makeup cosmetics include aqueous mascara containing water, a water-soluble resin or oil-in-water (O/W) resin, and a thickener.

The medium can be determined appropriately depending on the type of the cosmetic. Examples of the medium include: ketones that are in the form of liquid at room temperature, such as methyl ethyl ketone, methyl isobutyl ketone, diisobutyl ketone, isophorone, cyclohexanone and acetone; alcohols that are in the form of liquid at room temperature, such as ethanol, isopropanol, diacetone alcohol, 2-butoxyethanol and cyclohexanol; glycols that are in the form of liquid at room temperature, such as ethylene glycol, propylene glycol, pentylene glycol and glycerol; propylene glycol ethers that are in the form of liquid at room temperature, such as propylene glycol monomethyl ether, propylene glycol monomethyl ether acetate, and dipropylene glycol mono-n-butyl ether; short chain esters with 3 to 8 carbon atoms such as ethyl acetate, methyl acetate, propyl acetate, n-butyl acetate and isopentyl acetate; alkanes that are in the form of liquid at room temperature, such as decane, heptane, dodecane and cyclohexane; and cyclic aromatic compounds that are in the form of liquid at room temperature, such as toluene and xylene. In particular, ethanol and short chain esters are preferred in terms of safety to human bodies.

The cosmetic of the present invention may contain moisturizing agents, solid oils, liquid oils and/or powders as needed.

Examples of the moisturizing agents include polyethylene glycol, propylene glycol, glycerin, 1,3-butylene glycol, hexylene glycol, xylitol, sorbitol, maltitol, chondroitin sulfate, mucoitinsulfuric acid, caronic acid, atelocollagen, cholesteryl-12-hydroxy stearate, sodium lactate, bile salt, dl-pyrrolidone carboxylate, diglycerol (EO) PO adduct, chestnut rose extract, yarrow extract, and melilot extract.

Examples of the solid oils include: hydrocarbons such as polyethylene wax, ethylene propylene copolymer, solid paraffin wax, ceresin wax, microcrystalline wax, Fischer-Tropsch wax, and montan wax; waxes such as carnauba wax, candelilla wax, beeswax, Japan wax and spermaceti; fats and oils such as cocoa butter, palm oil and beef tallow; higher fatty acids such as stearic acid, lauric acid, myristic acid and behenic acid; higher alcohols such as cetyl alchohol, stearyl alcohol, lauryl alcohol and behenyl alcohol; hydrogenated oils such as hydrogenated coconut oil and hydrogenated castor oil; esters such as methyl stearate, cetyl palmitate, pentaerythritol rosinate and propylene glycol distearate; and silicone waxes such as stearyl-modified polysiloxane and behenyl-modified polysiloxane. These solid oils may be used in a combination of two or more.

Irrespective of the origin such as animal oil, vegetable oil or synthetic oil, examples of the liquid oils include hydrocarbons, fats and oils, hydrogenated oils, ester oils, aliphatic acids, higher alcohols, silicone oils, fluorine-based oils, lanolin derivatives, oil-based gelling agents, lipophilic surfactants and oil-soluble UV absorbers. Specific examples of the liquid oils include: hydrocarbons such as liquid paraffin, squalane, vaseline, polyisobutylene and polybutene; fats and oils such as olive oil, castor oil, jojoba oil, mink oil and Macadamia nut oil; esters such as cetyl isooctanate, isopropyl myristate, isopropyl palmitate, octyldodecyl myristate, glyceryl trioctanate, diglyceryl diisostearate, diglyceryl triisostearate, glyceryl tribehenate, pentaerythritol rosinate, neopentyl glycol dioctanate, cholesterol fatty acid ester and di(cholesteryl-behenyl-octyldodecyl) N-lauroyl-L-glutamate; aliphatic acids such as isostearyl acid and oleic acid; higher alcohols such as oleyl alcohol and isostearic alcohol; silicones such as dimethylpolysiloxane oiligomer, dimethylpolysiloxane high polymer, methylphenyl polysiloxane, decamethyl cyclo pentasiloxane, octamethyl cyclo tetrasiloxane, polyether-modified polysiloxane, cross-linked organopolysiloxane, and fluorine-modified silicone; fluorine-based oils such as perfluoropolyether, perfluorodecane and perfluorooctane; lanoline derivatives such as lanoline acetate, lanoline fatty acid isopropyl and lanoline alcohol; oil-based gelling agents such as dextrin fatty acid ester, sucrose fatty acid ester, starch fatty acid ester, aluminum 12-hydroxystearate, and calcium stearate; and oil-soluble UV absorbers such as ethyl para-aminobenzoate, p-methoxycinnamic-2-ethylhexyl, 4-tert-butyl-4'-methoxydibenzoylmethane and oxybenzone. These liquid oils may be used in a combination of two or more.

Examples of the powders include inorganic powders, bright powders, organic powders, dye powders and composite powders. These powders may be used in a combination of two or more, and may be surface treated with, for example, metal oxide, metal hydroxide, a fluorine compound, silicone oil, metallic soap, wax, fats and oils, or hydrocarbon. Powders may have any shape including spherical, plate and needle shapes. The average particle diameter of the powders may be smaller than or as large as the average particle diameter of the interference pigment of the present invention, but preferably 0.05 μm to 50 μm, more preferably 0.05 μm to 10 μm, for the purpose of obtaining favorable flexibility and favorable feeling in use. Further, the powders may have either a porous or nonporous structure.

Examples of the inorganic powders include titanium oxide powder, black titanium oxide powder, iron blue powder, ultramarine blue powder, red iron oxide powder, yellow iron oxide powder, black iron oxide powder, zinc oxide powder, aluminum oxide powder, magnesium oxide powder, zirconium oxide powder, magnesium carbonate powder, calcium carbonate powder, chromium oxide powder, chromium hydroxide powder, carbon black powder, aluminum silicate powder, magnesium silicate powder, aluminum-magnesium silicate powder, mica powder, synthetic mica powder, synthetic sericite powder, sericite powder, talc powder, kaoline powder, silicic anhydride powder, silica bead powder, silicon carbide powder, barium sulfate powder, bentonite powder, smectite powder, and boron nitride powder.

Examples of the bright powders include bismuth oxychloride powder, natural mica-titanium powder (natural mica coated with titanium dioxide), natural mica powder coated with iron oxide, natural mica-titanium powder coated with iron oxide, natural mica-titanium powder treated with an organic pigment, and aluminum powder.

Examples of the organic powders include nylon powder, polymethyl methacrylate, acrylonitrile-methacryl copolymer powder, vinylidene chloride-methacrylic acid copolymer powder, polystyrene powder, polymethyl celsesquioxane powder, organopolysiloxane elastomer powder, urethane powder, wool powder, silk powder, crystalline cellulose, and N-acyllysine.

Examples of the dye powders include an organic tar-based pigment and a lake pigment of organic dye.

Examples of the composite powders include reduced titanium natural mica powder coated with titanium oxide fine particles, titanium natural mica powder coated with zinc oxide fine particles, titanium natural mica powder coated with barium sulfate, titanium oxide-containing silicon dioxide powder, and zinc oxide-containing silicon dioxide powder.

The cosmetic of the present invention may further contain a surfactant, an antioxidant, perfume, a preservative, water, polyhydric alcohol such as glycerin and 1,3-butylene glycol, lower alcohol, and/or a beauty component as needed.

Although the preferred content of the interference pigment of the present invention in the cosmetic has been described above, the content of each component in the cosmetic is not limited in the present invention and it may be similar to that in a variety of conventionally known cosmetics.

Hereinafter, the present invention is described in further detail by way of examples and comparative examples. However, the present invention is not limited to the following description.

EXAMPLES

<Preparation of Interference Pigment>

Interference pigments of Examples 1-4 and pigments of Comparative Examples 1-4 were prepared in the following manner. In Examples 1 and 2, an inorganic substrate was coated with a transparent metal layer and a metal oxide layer in this order (configuration of FIG. 1). In Examples 3 and 4, an inorganic substrate was coated with a metal oxide layer, a transparent metal layer, and a metal oxide layer in this order (configuration of FIG. 2). In Comparative Examples 1 and 2, a marketed pigment (without transparent metal layer) in which an inorganic substrate is coated with a metal oxide layer was prepared. In Comparative Example 3, a pigment was prepared in the same manner as in Example 3 except that a transparent metal layer was not formed. In Comparative Example 4, a pigment was prepared in the same manner as in Example 3 except that a metal oxide layer was not formed.

Example 1

Au+Titanium Oxide

The surface of a flaky transparent glass substrate was coated with a gold layer as described below, and the surface was further coated with a rutile titanium oxide to produce an interference pigment of Example 1.

[Pretreatment Step of Flaky Glass Substrate]

1.2 kg of flaky glass substrate (average particle diameter: 80 μm, average thickness: 1.3 μm) was added to 8.4 L of ion-exchanged water and they were stirred by a stirrer. During the stirring, dilute hydrochloric acid was added thereto to adjust the pH to 2.5 to obtain a slurry. After adding 1.7 L of an aqueous solution of 0.5 mass % tin(II) chloride at room temperature to the obtained slurry, the pH was adjusted to 2.5 with dilute hydrochloric acid to obtain a mixture slurry. The mixture slurry was stirred for 5 minutes, and then filtered under reduced pressure to collect the flaky glass substrate. The flaky glass substrate collected was washed with ion-exchanged water to obtain a flaky glass substrate pretreated with tin.

[Metal Coating Step]

8.4 L of ion-exchanged water was heated to 75° C. while being stirred. 6 g of sodium gold sulfite was added to the heated ion-exchanged water, and it was stirred at 75° C. to dissolve the sodium gold sulfite. 1.2 kg of the pretreated flaky glass substrate was dispersed therein to obtain a suspension. 12 g of an aqueous solution of 3% sodium L-ascorbate was added to the obtained suspension, and it was stirred for 15 minutes and filtered under reduced pressure to collect solids (product) in the suspension. The solids collected were washed with ion-exchanged water.

After being dried at a constant temperature of 180° C., the solids were calcined in an electric heating furnace at 450° C. for two hours. Thus, a pigment in which the surface of the glass substrate was coated with gold layer was obtained.

[Metal Oxide Coating Step]

The pigment in which the surface of the glass substrate was coated with gold layer (hereinafter, also referred to as a "gold-coated glass substrate") was subjected to the following treatment.

Ion-exchanged water was added to 1.2 kg of the gold-coated glass substrate so that the total volume would be 12 L, and they were stirred by a stirrer. During the stirring, dilute hydrochloric acid was added thereto to adjust the pH to 1.5 to obtain a slurry. After adding 1.6 L of an aqueous solution of 0.7 mass % tin(IV) chloride at room temperature to the obtained slurry, the pH was adjusted to 1.5 with dilute hydrochloric acid to obtain a mixture slurry. The mixture slurry was stirred for 5 minutes, and then filtered under reduced pressure to collect the flaky glass substrate. The flaky glass substrate collected was washed with ion-exchanged water to obtain a flaky glass substrate pretreated with tin.

Ion-exchanged water was added to 1.2 kg of the gold-coated glass substrate treated with tin so that the total volume would be 12 L. The mixture was then heated to 75° C. while adjusting the pH to 1.0 with 35 mass % hydrochloric acid. During stirring, an aqueous solution of titanium tetrachloride (containing 16.5 mass % of titanium) was quantitatively added thereto at a rate of 290 g/hour while an aqueous solution of 10 mass % sodium hydroxide was added thereto at a rate of 1.4 L/hour. The addition of the aqueous solution of titanium tetrachloride and the addition of the aqueous solution of sodium hydroxide were continued to form a rutile titanium oxide layer with a bright red pearl tone on the gold layer. Thereafter, it was filtered under reduced pressure to collect the gold-coated glass substrate on which a titanium oxide layer was formed. The gold-coated glass substrate collected was washed with ion-exchanged water, dried at 180° C., and then calcined at 450° for two hours to obtain an interference pigment of Example 1.

The interference pigment of Example 1 thus obtained exhibited pale pink on a white paper and red interference color on a black paper.

Example 2

Au+Titanium Oxide

The interference pigment of Example 2 was obtained in the same manner as in Example 1 via the pretreatment step, the metal coating step, and the metal oxide coating step, except that the addition of the aqueous solution of titanium tetrachloride and the addition of the aqueous solution of sodium hydroxide were continued until a rutile titanium oxide layer with a blue pearl tone was formed.

The interference pigment of Example 2 thus obtained exhibited pale blue on a white paper and blue interference color on a black paper.

Example 3

Titanium Oxide+Au+Titanium Oxide

The interference pigment of Example 3 was obtained in the same manner as in Example 1 via the pretreatment step, the metal coating step, and the metal oxide coating step, except that a marketed bright pigment (METASHINE (registered trademark) MT1080RB manufactured by Nippon Sheet Glass Co., Ltd.) was used instead of the flaky transparent glass substrate. METASHINE (registered trademark) MT1080RB is a pigment in which the surface of a flaky transparent glass substrate is coated with a rutile titanium oxide with a blue pearl tone. The average particle diameter of METASHINE (registered trademark) MT1080RB is 85 µm, and the thickness of the glass substrate contained therein is 1.3 µm.

The interference pigment of Example 3 thus obtained exhibited pale pink on a white paper and pink interference color on a black paper.

METASHINE (registered trademark) MT1080RB can be produced in the following process, for example.

Ion-exchanged water was added to 1.2 kg of a flaky glass substrate (average particle diameter: 80 µm, average thickness: 1.3 µm) so that the total volume would be 12 L, and they were stirred by a stirrer. During the stirring, dilute hydrochloric acid was added thereto to adjust the pH to 1.5 to obtain a slurry. After adding 1.6 L of an aqueous solution of 0.7 mass % tin(IV) chloride at room temperature to the obtained slurry, the pH was adjusted to 1.5 with dilute hydrochloric acid to obtain a mixture slurry. The mixture slurry was stirred for 5 minutes, and then filtered under reduced pressure to collect the flaky glass substrate. The flaky glass substrate collected was washed with ion-exchanged water to obtain a flaky glass substrate pretreated with tin.

Ion-exchanged water was added to 1.2 kg of the glass substrate treated with tin so that the total volume would be 12 L. The mixture was then heated to 75° C. while adjusting the pH to 1.0 with 35 mass % hydrochloric acid. During stirring, an aqueous solution of titanium tetrachloride (containing 16.5 mass % of titanium) was quantitatively added thereto at a rate of 290 g/hour while an aqueous solution of 10 mass % sodium hydroxide was added thereto at a rate of 1.4 L/hour. The addition of the aqueous solution of titanium tetrachloride and the addition of the aqueous solution of sodium hydroxide were continued to form a rutile titanium oxide layer with a bright blue pearl tone on the glass substrate. Thereafter, it was filtered under reduced pressure to collect the flaky glass substrate on which a titanium oxide layer was formed. The glass substrate collected was washed with ion-exchanged water, dried at 180° C., and then calcined at 450° for two hours. Thus, a pigment in which the surface of a flaky transparent glass substrate is coated with a rutile titanium oxide with a blue pearl tone can be obtained.

Example 4

Titanium Oxide+Ag+Au+Titanium Oxide

The surface of the marketed bright pigment (METASHINE (registered trademark) MT1080RB manufactured by Nippon Sheet Glass Co., Ltd.) was coated with a silver layer and a gold layer in this order, and further coated with a rutile titanium oxide to produce the interference pigment of Example 4.

First, the pretreatment step was performed with respect to the marketed bright pigment in the same manner as in Example 1.

[Metal Layer Coating Step]

8.4 L of ion-exchanged water was heated to 30° C. while being stirred, into which 1.2 kg of the pretreated bright pigment was dispersed to obtain a suspension. 0.8 g of silver nitrate was dissolved in ion-exchanged water adjusted at pH 2.5, and the dissolution was added to the obtained suspension, followed by stirring for 10 minutes. Then, it was filtered under reduced pressure to collect solids (product) in the suspension. The solids collected were washed with ion-exchanged water. Thereby, a silver layer was formed on the surface of the rutile titanium oxide layer, and thus a bright pigment whose surface is coated with a silver layer was obtained.

8.4 L of ion-exchanged water was heated to 75° C. while being stirred, into which 6 g of sodium gold sulfite was dissolved. 1.2 kg of the bright pigment coated with silver layer was dispersed in the solution to obtain a suspension. 12 g of an aqueous solution of 3% sodium L-ascorbate was added to the obtained suspension, and it was stirred for 15 minutes and filtered under reduced pressure to collect solids (product) in the suspension. The solids collected were washed with ion-exchanged water. After being dried at a constant temperature of 180° C., the solids were calcined in an electric heating furnace at 450° C. for two hours. Thus, a pigment in which the surface of the glass substrate was coated with the rutile titanium oxide layer, the silver layer, and the gold layer was obtained.

[Metal Oxide Coating Step]

The interference pigment of Example 4 was obtained by performing the rutile titanium oxide coating step in the same manner as in Example 1 with respect to the pigment obtained in the above metal layer coating step.

The interference pigment of Example 4 thus obtained exhibited pale pink on a white paper and pink interference color on a black paper.

Comparative Example 1

In Comparative Example 1, a marketed bright pigment (METASHINE (trade mark) MT1080RR (Nippon Sheet Glass Co., Ltd.)) with a red pearl tone was used. METASHINE (trade mark) MT1080RR is a pigment in which the surface of a flaky transparent glass substrate is coated with a rutile titanium oxide with a red pearl tone. The average particle diameter of METASHINE (trade mark) MT1080RR is 85 µm, and the thickness of the glass substrate contained therein is 1.3 µm.

METASHINE (trade mark) MT1080RR can be obtained in the same manner as in the production process of METASHINE (trade mark) MT1080RB described above, except that the addition of the aqueous solution of titanium tetrachloride and the addition of the aqueous solution of sodium hydroxide were continued until a ruffle titanium oxide layer with a red pearl tone was formed.

Comparative Example 2

In Comparative Example 2, a marketed bright pigment (METASHINE (trade mark) MT1080RB manufactured by Nippon Sheet Glass Co., Ltd.) was prepared.

Comparative Example 3

The pigment of Comparative Example 3 was obtained in the same manner as in Example 3 except that the metal layer coating step was not performed.

Comparative Example 4

The pigment of Comparative Example 4 was obtained in the same manner as in Example 3 except that the metal oxide coating step was not performed. The reflection of the gold layer of the obtained pigment was strong. When applied to a white paper, the pigment hid the base color because the color of the pigment itself was too strong. The development of pale colors was not achieved.

The interference pigments of Examples 1-4 and the pigments of Comparative Examples 1-4 produced in the above-described manner were subjected to the following measurements in the manners described below: the average particle diameter, the average thickness, the CIE 1976 (L*a*b*) color system, the visible light transmittance, the visible light reflectance, the metal content in the transparent metal layer, the thickness of the transparent metal layer, and the thickness of the metal oxide layer. Tables 5 and 6 below show the results.

(1) Average Particle Diameters of the Glass Substrate (inorganic Substrate) and the Interference Pigment The particle diameter of the inorganic substrate or pigment was measured with a laser diffraction particle diameter distribution analyzer (trade name: "MICROTRAC BRA", manufactured by NIKKISO CO., LTD), and a particle diameter (D50) that corresponds to a particle diameter at which the cumulative volume of particles reaches 50% in the particle diameter distribution was determined as an average particle diameter of the inorganic substrate or pigment.

(2) Average Thickness of the Inorganic Substrate

The average thickness of the inorganic substrate was determined by measuring the thicknesses of 100 inorganic substrate grains and averaging the thicknesses. The thickness of each inorganic substrate was calculated by measuring an optical-path difference between direct light (light not influenced by a phase object) and light passed through the inorganic substrate, with use of an interference microscope (trade name: INTERPHAKO, manufactured by Carl Zeiss Jena).

(3) CIE 1976 (L*a*b*) Color System 1 g of each of the interference pigments of Examples 1-4 and the pigments of Comparative Examples 1-4 was blended with 9 g of an acrylic lacquer (Acrylic Auto Clear Super, manufactured by NIPPON PAINT Co., Ltd.) and mixed thoroughly. The mixture was applied to the surface of a hiding chart in a coating thickness of 9 mils, and dried naturally at a room temperature to prepare each evaluation sample.

For comparison, an acrylic resin not containing a pigment (acrylic lacquer (Acrylic Auto Clear Super, manufactured by NIPPON PAINT Co., Ltd.)) was applied to the surface of a hiding chart in a coating thickness of 9 mils, and dried naturally at a room temperature to prepare a blank.

The white parts of the evaluation samples and blank were measured according the CIE 1976 (L*a*b*) color system using a chroma meter (manufactured by Konica Minolta Inc.) to calculate color differences ΔE of the respective evaluation samples with respect to the blank, from the formula below. The color differences ΔE obtained are indicated in Table 6 below.

$$\Delta E = ((Ls-L1)^2 + (as-a1)^2 + (bs-b1)^2)^{1/2}$$

Ls, as, bs: Lab values of the blank

L1, a1, b1: Lab values in examples and comparative examples (4) Visible Light Transmittance The visible light transmittances of the interference pigments of Examples 1-4 and the pigments of Comparative Examples 1-4 were measured in accordance with the procedure below.

[Preparation of Samples]

1.0 g of each of the interference pigments of Examples 1-4 and the pigments of Comparative Examples 1-4 was mixed with 9.0 g of an acrylic resin, and the mixture was applied to the surface of a PET film in a coating thickness of 9 mils. Then, it was dried naturally for two hours, and dried at 80° C. for 10 minutes to prepare each sample.
[Measurement Method]

The transmittances of lights at wavelengths of 480 nm, 580 nm and 680 nm (Table 6) of each sample were measured using a near-infrared ultraviolet and visible spectrophotometer (trade name: UV-3600, manufactured by Shimadzu Corporation). For baseline correction, a reference was used that was prepared by applying an acrylic resin not containing a pigment to the surface of a PET film in a coating thickness of 9 mils, drying it naturally for two hours, and drying it at 80° C. for 10 minutes.

(5) Visible Light Reflectance

The visible light reflectances of the interference pigments of Examples 1-4 and the pigments of Comparative Examples 1-4 were measured in accordance with the procedure below.
[Preparation of Samples]

1.0 g of each of the interference pigments of Examples 1-4 and the pigments of Comparative Examples 1-4 was mixed with 9.0 g of an acrylic resin, and the mixture was applied to the surface of a hiding chart in a coating thickness of 9 mils. Then, it was dried naturally for two hours, and dried at 80° C. for 10 minutes to prepare each sample.
[Measurement Method]

The light reflectances at wavelengths of 480 nm, 580 nm and 680 nm (Table 6) of the white parts of the hiding charts were measured using a near-infrared ultraviolet and visible spectrophotometer (trade name: UV-3600, manufactured by Shimadzu Corporation). For baseline correction, a barium sulphate belonging to the spectrophotometer was used as a standard plate.

(6) Metal Content in the Transparent Metal Layer with Respect to the Total Weight of the Transparent Metal Layer and the Object Coated with the Transparent Metal Layer Using the pigments obtained in the metal layer coating step of Examples 1-4 and Comparative Example 4 (pigments before the metal oxide layer coating step) as samples, the amount of the metal (gold or silver) contained in the metal layer of each pigment was measured in accordance with the procedures below, and the amount of the metal (gold, or silver and gold) per sample (weight) was calculated using the measured value to determine the metal content in the transparent metal layer with respect to the total weight of the transparent metal layer and the object coated with the transparent metal layer.

<Gold Layer>
[Preparation of Measurement Solution]

To 2.5 g of each sample (pigment in which gold layer was formed), 5 ml of aqua regia was added, and 15 ml of water was added further. After heating at 125° C. for two hours or more, the solution was cooled and filtered using a paper filter. A precipitate obtained was washed several times with a small amount of water, and water was added to the washed precipitate to obtain 50 ml of a measurement solution.

[Measurement Method]

The measurement solution obtained was measured with an ICP emission spectroscopy (trade name: ICPS-7510, manufactured by Shimadzu Corporation) to measure the amount of the gold contained in the measurement solution. The coating amount of the gold was calculated from the formula below using the measured value, and the value obtained was determined as the gold content (mass %) in the gold layer.

Metal(ppm)=measured value (ppm)×50 (ml)/sample weight (g)

<Silver Layer>
[Preparation of Measurement Solution]

To 0.1 g of each sample (pigment in which silver layer was formed), 20 ml of water was added, and 5 ml of nitric acid (1+1) was added. After dissolution by heating, the solution was cooled and filtered using a paper filter. A precipitate obtained was washed thoroughly with nitric acid, and water was added to the washed precipitate to obtain 100 ml of a measurement solution.

[Measurement Method]

The measurement solution obtained was measured with an ICP emission spectroscopy (trade name: ICPS-7510, manufactured by Shimadzu Corporation), and the coating amount of the silver was calculated from the formula below. The value obtained was determined as the silver content (mass %).

Metal (ppm)=measured value (ppm)×100 (ml)/ sample weight (g)

(7) Thickness of Metal Layer

Using the pigments obtained in the metal layer coating step of Examples 1-4 and Comparative Example 4 as samples, the thicknesses of the metal layers were measured. The thicknesses of the metal layers of Examples 1 and 2 were measured using the calculation formula indicated in Table 2 below, the thicknesses of the metal layers of Example 3 and Comparative Example 4 were measured using the calculation formula indicated in Table 3 below, and the thickness of the metal layer of Example 4 was measured using the calculation formula indicated in Table 4 below. The calculation was performed using the weight of the metal layer per sample and the surface area of an object on which the metal layer is formed based on 100 g of the pigments of Example 1-4. As to the interference pigments of Examples 1 and 2, since the metal layer coats the surface of the inorganic substrate, the thickness of the metal layer was calculated using the surface area of the inorganic substrate. As to the interference pigments of Examples 3 and 4, since the metal layer coats the surface of the metal oxide layer that coats that inorganic substrate, the thickness of the metal layer was calculated using the surface area of the inorganic substrate coated with the metal oxide layer.

(8) Thicknesses of Interference Pigment and Metal Oxide Layer

The thicknesses of the interference pigment and the metal oxide layer were determined by measuring the thicknesses of the cross sections (10 points) of the interference pigment at 100000× magnification with use of a field emission scanning electron microscope (FE-SEM) (trade name: S-4700, manufactured by Hitachi High-Technologies), and averaging the thicknesses.

TABLE 2

|  |  |  | Calculation Formula | Example 1 | Example 2 |
|---|---|---|---|---|---|
| Substrate | Specific gravity | g/μm$^3$ | — | $2.65 \times 10^{-12}$ | $2.65 \times 10^{-12}$ |
|  | Diameter D | μm | — | 80 | 80 |
|  | Thickness L | μm | — | 1.3 | 1.3 |
|  | Volume/each V | μm$^3$ | $\pi \times (D/2)^2 \times L$ | $6.5345 \times 10^3$ | $6.5345 \times 10^3$ |

TABLE 2-continued

|  |  |  |  | Calculation Formula | Example 1 | Example 2 |
|---|---|---|---|---|---|---|
| | Surface area/each | S | $\mu m^2$ | $\pi \times D \times L + \pi \times (D/2)^2 \times 2$ | $1.0380 \times 10^4$ | $1.0380 \times 10^4$ |
| | Weight/each | H | g | V × Specific gravity of substrate | $1.7316 \times 10^{-8}$ | $1.7316 \times 10^{-8}$ |
| | Weight | F | g | 100 g − M | 99.96 | 99.94 |
| Metal layer | Weight | M | g | 100 g × Content (mass %)/100 | 0.04 | 0.06 |
| | Weight/each | A | g | M/(F/H) | $6.9294 \times 10^{-12}$ | $1.0396 \times 10^{-11}$ |
| | Specific gravity of metal (gold) | G | $g/\mu m^3$ | — | $1.932 \times 10^{-11}$ | $1.932 \times 10^{-11}$ |
| | Thickness | | nm | $A/(S \times G) \times 10^3$ | 0.035 | 0.052 |

TABLE 3

|  |  |  |  | Calculation Formula | Example 3/ Comparative Example 4 |
|---|---|---|---|---|---|
| Substrate | Specific gravity | | $g/\mu m^3$ | — | $2.65 \times 10^{-12}$ |
| | Diameter | D | $\mu m$ | — | 80 |
| | Thickness | L | $\mu m$ | — | 1.3 |
| | Volume/each | V | $\mu m^3$ | $\pi \times (D/2)^2 \times L$ | $6.5345 \times 10^3$ |
| | Weight/each | H | g | V × Specific gravity of substrate | $1.7316 \times 10^{-8}$ |
| Metal oxide layer (Titanium oxide layer) | Specific gravity | | $g/\mu m^3$ | — | $4.260 \times 10^{-12}$ |
| | Weight/each | T | g | (V1 − V) × Specific gravity of titanium oxide | $1.1324 \times 10^{-8}$ |
| Sample (Substrate+ Metal oxide layer + Metal layer) | Diameter | D1 | $\mu m$ | — | 85 |
| | Thickness | L1 | $\mu m$ | — | 1.6 |
| | Surface area/each | S1 | $\mu m^2$ | $\pi \times D1 \times L1 + \pi \times (D1/2)^2 \times 2$ | $1.1782 \times 10^4$ |
| | Volume/each | V1 | $\mu m^3$ | $\pi \times (D1/2)^2 \times L1$ | $9.192 \times 10^3$ |
| Substrate+ Metal oxide layer | Weight/each | H1 | g | H + T | $2.8640 \times 10^{-8}$ |
| | Weight | F1 | g | 100 g − M1 | 99.95 |
| Metal layer | Weight of metal layer | M1 | g | 100 g × Content (mass %)/100 | 0.05 |
| | Weight/each | A | g | M1/(F1/H1) | $1.4327 \times 10^{-11}$ |
| | Specific gravity of metal (gold) | G | $g/\mu m^3$ | — | $1.932 \times 10^{-11}$ |
| | Thickness | | nm | $A/(S1 \times G) \times 10^3$ | 0.063 |

TABLE 4

|  |  |  |  | Calculation Formula | Example 4 |
|---|---|---|---|---|---|
| Substrate | Specific gravity | | $g/\mu m^3$ | — | $2.65 \times 10^{-12}$ |
| | Diameter | D | $\mu m$ | — | 80 |
| | Thickness | L | $\mu m$ | — | 1.3 |
| | Volume/each | V | $\mu m^3$ | $\pi \times (D/2)^2 \times L$ | $6.5345 \times 10^3$ |
| | Weight/each | H | g | V × Specific gravity of substrate | $1.7316 \times 10^{-8}$ |
| Metal oxide layer (Titanium oxide layer) | Specific gravity | | $g/\mu m^3$ | — | $4.260 \times 10^{-12}$ |
| | Weight/each | T | g | (V1 − V) × Specific gravity of titanium oxide | $1.1324 \times 10^{-8}$ |
| Sample (Substrate + Metal oxide layer + Metal layer) | Diameter | D1 | $\mu m$ | — | 85 |
| | Thickness | L1 | $\mu m$ | — | 1.6 |
| | Surface area/each | S1 | $\mu m^2$ | $\pi \times D1 \times L1 + \pi \times (D1/2)^2 \times 2$ | $1.1782 \times 10^4$ |
| | Volume/each | V1 | $\mu m^3$ | $\pi \times (D1/2)^2 \times L1$ | $9.192 \times 10^3$ |
| Substrate + | Weight/each | H1 | g | H + T | $2.8640 \times 10^{-8}$ |

TABLE 4-continued

|  |  |  |  | Calculation Formula | Example 4 |
|---|---|---|---|---|---|
| Metal oxide layer | Weight | F1 | g | 100 g − M1 − M2 | 99.93 |
| Metal layer | Gold layer | Weight of gold layer | M1 | g | 100 g × Content (mass %)/100 | 0.04 |
|  |  | Weight of gold layer/each | A1 | g | M1/(F1/H1) | $1.1464 \times 10^{-11}$ |
|  |  | Specific gravity of metal (gold) | G1 | g/μm³ | — | $1.932 \times 10^{-11}$ |
|  |  | Thickness of gold layer |  | nm | A1/(S1 × G1) × $10^3$ | 0.050 |
|  | Silver layer | Weight of silver layer | M2 | g | 100 g × Content (mass %)/100 | 0.03 |
|  |  | Weight of silver layer/each | A2 | g | M2/(F1/H1) | $8.5981 \times 10^{-12}$ |
|  |  | Specific gravity of metal (silver) | G2 | g/μm³ | — | $1.051 \times 10^{-11}$ |
|  |  | Thickness of silver layer |  | nm | A2/(S1 × G2) × $10^3$ | 0.069 |

TABLE 5

|  |  | First metal oxide layer | Transparent metal layer | | | Second metal oxide layer | Pigment | |
|---|---|---|---|---|---|---|---|---|
|  |  | Thickness (nm) | Material | Content (mass %) | Thickness (nm) | Thickness (nm) | Average particle diameter (μm) | Average thickness (μm) |
| Example | 1 | 124 | Gold | 0.04 | 0.035 | — | 85 | 1.55 |
|  | 2 | 150 | Gold | 0.06 | 0.052 | — | 86 | 1.60 |
|  | 3 | 91 | Gold | 0.05 | 0.063 | 151 | 83 | 1.78 |
|  | 4 | 90 | Silver | 0.03 | 0.069 | 151 | 84 | 1.78 |
|  |  |  | Gold | 0.04 | 0.050 |  |  |  |
| Comparative Example | 1 | 122 | — | — | — | — | 85 | 1.54 |
|  | 2 | 147 | — | — | — | — | 86 | 1.59 |
|  | 3 | 89 | — | — | — | 151 | 83 | 1.78 |
|  | 4 | — | Gold | 0.05 | 0.063 | 151 | 86 | 1.60 |

TABLE 6

|  |  | Film configuration | Base: white | | | | Reflectance (%) | | | Transmittance (%) | | |
|---|---|---|---|---|---|---|---|---|---|---|---|---|
|  |  |  | L* | a* | b* | ΔE | 480 nm | 580 nm | 680 nm | 480 nm | 580 nm | 680 nm |
| Blank |  | black and white paper chart | 91.68 | −0.40 | 3.54 | — | 79.8 | 79.5 | 82.8 | — | — | — |
| Example | 1 | Gold/Titanium oxide | 87.04 | 0.22 | 0.15 | 5.8 | 73.8 | 67.3 | 72.6 | 86.5 | 79.7 | 61.4 |
|  | 2 | Gold/Titanium oxide | 86.58 | −0.08 | −0.46 | 6.5 | 68.6 | 68.1 | 75.3 | 54.0 | 86.0 | 85.6 |
|  | 3 | Titanium oxide/Gold/Titanium oxide | 82.55 | 7.17 | −2.53 | 13.3 | 66.1 | 59.5 | 73.7 | 78.8 | 55.4 | 57.0 |
|  | 4 | Titanium oxide/Silver + Gold/Titanium oxide | 81.60 | 5.80 | −2.10 | 13.1 | 65.3 | 55.7 | 70.8 | 80.4 | 58.9 | 61.2 |
| Comparative Example | 1 | Titanium oxide | 90.74 | −1.14 | 3.09 | 1.3 | 79.2 | 76.0 | 75.8 | 84.2 | 77.2 | 58.1 |
|  | 2 | Titanium oxide | 91.09 | −0.20 | 3.77 | 0.7 | 73.3 | 79.2 | 81.5 | 54.7 | 88.0 | 86.8 |
|  | 3 | Titanium oxide/Titanium oxide | 90.37 | −0.56 | 2.38 | 1.8 | 78.5 | 73.3 | 76.4 | 81.4 | 64.0 | 63.4 |

TABLE 6-continued

| Film configuration | Base: white | | | | Reflectance (%) | | | Transmittance (%) | | |
|---|---|---|---|---|---|---|---|---|---|---|
| | L* | a* | b* | ΔE | 480 nm | 580 nm | 680 nm | 480 nm | 580 nm | 680 nm |
| 4 Titanium oxide/Gold | 85.03 | 3.42 | 1.26 | 8.0 | 65.2 | 68.0 | 78.4 | 51.4 | 84.9 | 86.8 |

[Evaluation]

(1) Comparison of Color Measurement Data

When the color differences ΔE of Examples 1 and 2 and the color differences ΔE of Comparative Examples 1 and 2 are compared, the ΔE of the pigments of Comparative Examples 1 and 2 was less than 2, whereas the ΔE of the interference pigments of Examples 1 and 2 exceeded 2, as indicated in Table 6. This means that the color tones of the interference pigments of Examples 1 and 2 were largely different from that of the blank (pigment) in the white base, and thus interference colors could be measured. In the pigments of Comparative Examples 1 and 2, since light reflected at the base (white) cancelled the interference of light reflected at the surface of the rutile titanium oxide layer or the surface of the glass substrate, most of interference colors were hardly developed and could not be measured (their color tones were not different from that of the blank). On the other hand, in the interference pigments of Examples 1 and 2, the gold coating formed between the rutile titanium oxide layer and the glass substrate absorbed part of the light reflected at the base (white) and thus weakened the force of cancelling light interference by the light reflected at the base. As a result, interference colors were sufficiently developed to be measured. This indicates that the interference pigments of Examples 1 and 2 can develop vivid interference colors even when the base color is white, by including the metal layer between the rutile titanium oxide layer and the glass substrate.

When the ΔE of Examples 3 and 4 and the ΔE of Comparative Example 3 are compared, the ΔE of the pigment of Comparative Example 3 was less than 2, whereas the ΔE of the interference pigments of Examples 3 and 4 exceeded 10, as indicated in Table 6. Moreover, the ΔE of the interference pigments of Examples 3 and 4 was significantly larger than the ΔE of the interference pigments of Examples 1 and 2. This indicates that the interference pigments of Examples 3 and 4, in which the ruffle titanium oxide layer was arranged between the gold layer or the gold layer and silver layer and the glass substrate, and the glass substrate was coated with the rutile titanium oxide layer, the gold layer or the gold layer and silver layer, and the rutile titanium oxide layer in this order, can develop vivider interference colors.

The ΔE of the pigment of Comparative Example 4 was 8.0, which is relatively high. The reason for this is that since the outermost layer of the pigment was the gold layer, reflection of the gold layer looked strong. The color of the pigment of Comparative Example 4 itself was too strong and hid the base color when the base color was white.

Furthermore, as to the interference pigments of Examples 1 to 4, the base color can be seen through the interference pigment. Because of this, according to the interference pigments of Examples 1 to 4, the base color that can be seen through the interference pigment is mixed with the interference color expressed by the interference pigment. Thus, the interference pigments of Examples 1 to 4 can exhibit pale colors when used as the materials for cosmetics, paints, inks and resin compositions.

(2) Visible Light Reflectance

The visible light reflectances at wavelengths of 480 to 680 nm of the interference pigments of Examples 1, 2, and 3-4 are compared with those of the pigments of Comparative Examples 1, 2, and 3, respectively. The interference pigments of the Examples 1-4 containing the metal layer had lower visible light reflectance than the pigments of Comparative Examples 1-3 not containing the metal layer, as indicated in Table 6. This indicates that the metal layers contained in the interference pigments of Examples 1-4 and the metal layer contained in the pigment of Comparative Example 4 absorbed part of reflected light from the base.

(3) Visible Light Transmittance

The visible light transmittances of the interference pigments of Examples 1-4 exceeded 40% or more as indicated in Table 6, which are not much different from those of the pigments of Comparative Examples 1-4. This indicates that the formation of the gold layer or the gold layer and silver layer did not deteriorate the visible light transmittances of the interference pigments, and both of the formed gold layer and silver layer were transparent.

The above results indicate that the interference pigments of Examples 1-4 in which the inorganic substrate was coated with the metal layer and the metal oxide layer in this order can develop vivid interference colors even on the white base similarly to the black base because the metal layer moderately absorb part of the light reflected at the base.

Table 6 above also indicates that, since the interference pigments of Examples 1-4 and the pigment of Comparative Example 4 exhibited the same level of visible light transmittance as the pigments of Comparative Examples 1-3 even containing the metal layer, the metal layer did not deteriorate the visible light transmittance of the interference pigments. Moreover, since the interference pigments of Examples 1-4 exhibited sufficient visible light transmittance and vivid interference colors, the interference pigments of Examples 1-4 can develop pale interference colors, which are the mixtures of interference colors and the white base color.

Moreover, since the interference pigments of Examples 1-4 include a metal layer having an average thickness of 5 nm or less between the inorganic substrate and the metal oxide layer, part of reflected light from the base is moderately absorbed by the metal layer. Thus, the interference pigments of Examples 1-4 can develop vivider interference colors.

Moreover, the interference pigments of Examples 3 and 4, in which the surface of the inorganic substrate is coated with the metal oxide layer, the metal layer, and the metal oxide layer in this order, include more interfaces of layers formed from different materials, than the interference pigments of Examples 1 and 2. As a result, more reflection occurs at the interfaces, and more interference occurs in the interference pigments of Examples 3 and 4 than the interference pigments of Examples 1 and 2, thereby generating interference light with even stronger intensity. Therefore, the interference pigments of Examples 3 and 4, in which the surface of the inorganic substrate is alternately coated with the metal oxide layer and the metal layer, can develop even vivider interference colors.

Therefore, the interference pigments of Examples 1-4 can exhibit interference colors paler than conventional pigments. Therefore, the interference pigments of the present invention are useful as materials of pastel tone cosmetics with high texture (e.g., lipsticks, manicures, and eye shadows), paints, inks, and resin compositions for forming resin molded products.

(Application Examples of Cosmetics)
(Stick-Shaped Lipstick)

Stick-shaped lipsticks were produced using the interference pigments of Examples 1-4 and the pigments of Comparative Examples 1-4. Raw materials (A, B, and C) indicated in Table 8 below were added to a lipstick base (oily base) having the composition indicated in Table 7 below, followed by stirring and molding to produce each stick-shaped lipstick. The pastel-tone vividness of each lipstick was evaluated. Table 8 below shows the evaluation results. The compositions indicated in Table 8 were expressed in wt %.

<Production Method>

The respective raw materials indicated in Table 8 and the lipstick base having the composition indicated in Table 7 were placed in a stainless container and heated until the wax components, etc., were molten, and stirred uniformly by a stirrer and mixed. The mixture was then defoamed under reduced pressure, poured into a mold, and cooled to a room temperature to obtain each lipstick.

<Evaluation Method>

Sensory evaluation was performed by 20 panelists to determine the pastel-tone vividness of each lipstick on lips, based on the following evaluation criteria.

<Evaluation Criteria>

I: Fifteen or more out of twenty panelists answered that the pastel-tone vividness was favorable.
II: Ten to fourteen out of twenty panelists answered that the pastel-tone vividness was favorable.
III: Six to nine out of twenty panelists answered that the pastel-tone vividness was favorable.
IV: Five or less out of twenty panelists answered that the pastel-tone vividness was favorable.

TABLE 7

| Raw material | Weight % |
| --- | --- |
| Paraffin wax | 25 |
| Ceresin | 15 |
| Candelilla wax | 5 |
| Vaseline | 10 |
| Purified lanolin | 15 |
| Isotridecyl isononanoate | 12 |
| Dimethylpolysiloxane | 8 |
| Liquid paraffin | 10 |
| Total | 100 |

TABLE 8

| | | Example | | | | Comparative Example | | | |
| --- | --- | --- | --- | --- | --- | --- | --- | --- | --- |
| | | 5 | 6 | 7 | 8 | 5 | 6 | 7 | 8 |
| A | Pigment of Ex. 1 | 10 | — | — | — | — | — | — | — |
| | Pigment of Ex. 2 | — | 10 | — | — | — | — | — | — |
| | Pigment of Ex. 3 | — | — | 10 | — | — | — | — | — |
| | Pigment of Ex. 4 | — | — | — | 10 | — | — | — | — |
| | Pigment of Comp. Ex. 1 | — | — | — | — | 10 | — | — | — |
| | Pigment of Comp. Ex. 2 | — | — | — | — | — | 10 | — | — |
| | Pigment of Comp. Ex. 3 | — | — | — | — | — | — | 10 | — |
| | Pigment of Comp. Ex. 4 | — | — | — | — | — | — | — | 10 |
| B | Diisostearyl malate | 12 | 12 | 12 | 12 | 12 | 12 | 12 | 12 |
| C | Dimethicone polyol | 4 | 4 | 4 | 4 | 4 | 4 | 4 | 4 |
| | Lipstick base | 64 | 64 | 64 | 64 | 64 | 64 | 64 | 64 |
| | Red No. 202 | 4 | 4 | 4 | 4 | 4 | 4 | 4 | 4 |
| | Yellow No. 4 Al lake | 2 | 2 | 2 | 2 | 2 | 2 | 2 | 2 |
| | Particulate silica | 1 | 1 | 1 | 1 | 1 | 1 | 1 | 1 |
| | Titanium oxide | 2 | 2 | 2 | 2 | 2 | 2 | 2 | 2 |
| | Red iron oxide | 1 | 1 | 1 | 1 | 1 | 1 | 1 | 1 |
| | Pastel-tone vividness | I | I | I | I | IV | IV | III | III |

* Ex.: Example,
Comp. Ex.: Comparative Example

As is clear from Table 8 above, the stick-shaped lipsticks of Examples 5 to 8 exhibited excellent pastel-tone vividness.

(Lip Gloss)

Lip glosses were produced using the interference pigments of Examples 1-4 and the pigments of Comparative Examples 1-4. Specifically, respective raw materials indicated in Table 9 below were placed in a container, heated to 80° C., and stirred well. The obtained mixture was placed in a case to obtain each lip gloss. The compositions indicated in Table 9 were expressed based on the blended amount (parts by mass).

Next, the pastel-tone vividness of each lip gloss obtained was evaluated by twenty female panelists.

<Evaluation Criteria>

I: Fifteen or more out of twenty panelists answered that the pastel-tone vividness was favorable.
II: Ten to fourteen out of twenty panelists answered that pastel-tone the vividness was favorable.
III: Six to nine out of twenty panelists answered that the pastel-tone vividness was favorable.
IV: Five or less out of twenty panelists answered that the pastel-tone vividness was favorable.

TABLE 9

| | Example | | | | Comparative Example | | | |
| --- | --- | --- | --- | --- | --- | --- | --- | --- |
| | 9 | 10 | 11 | 12 | 9 | 10 | 11 | 12 |
| Dextrin palmitate | 3 | 3 | 3 | 3 | 3 | 3 | 3 | 3 |
| Hydrogenated polyisobutene | 20 | 20 | 20 | 20 | 20 | 20 | 20 | 20 |
| Isononyl isooctanoate | 10 | 10 | 10 | 10 | 10 | 10 | 10 | 10 |
| Squalane | 5 | 5 | 5 | 5 | 5 | 5 | 5 | 5 |
| Pigment of Ex. 1 | 10 | — | — | — | — | — | — | — |
| Pigment of Ex. 2 | — | 10 | — | — | — | — | — | — |
| Pigment of Ex. 3 | — | — | 10 | — | — | — | — | — |
| Pigment of Ex. 4 | — | — | — | 10 | — | — | — | — |
| Pigment of Comp. Ex. 1 | — | — | — | — | 10 | — | — | — |
| Pigment of Comp. Ex. 2 | — | — | — | — | — | 10 | — | — |
| Pigment of Comp. Ex. 3 | — | — | — | — | — | — | 10 | — |
| Pigment of Comp. Ex. 4 | — | — | — | — | — | — | — | 10 |
| Pastel-tone vividness | I | I | I | I | IV | IV | III | III |

* Ex.: Example,
Comp. Ex.: Comparative Example

As is clear from Table 9 above, the lip glosses of Examples 9 to 12 exhibited excellent pastel-tone vividness.

As described above, it is possible to provide cosmetics that can develop interference colors with pale color tones, by use of the interference pigments that include; a flaky inorganic substrate; a transparent metal layer that coats the inorganic substrate; and a metal oxide layer that coats the metal layer.

The invention claimed is:

1. An interference pigment comprising:
   a flaky inorganic substrate;
   a transparent metal layer that coats the inorganic substrate; and
   a metal oxide layer that coats an outer surface of the transparent metal layer and is in contact with the transparent metal layer;
   wherein the metal oxide layer is an outermost layer of the interference pigment,
   the metal oxide layer has an average thickness of 80 nm to 350 nm, and
   the metal oxide layer includes 99 atom % or more of rutile titanium oxide;
   the inorganic substrate comprises at least one material selected from the group consisting of glass, mica, silica, and alumina,
   the transparent metal layer is a metal selected from the group consisting of silver, gold, and an alloy of gold and silver;
   wherein the interference pigment has:
   a color difference ΔE with respect to a blank measured according to the CIE 1976 (L*a*b*) color system that is 4 or more and 20 or less, and
   a reflectance for light having a wavelength of 680 nm that is 60% or more and 75.5% or less.

2. The interference pigment according to claim 1, wherein, when the metal oxide layer is referred to as a first metal oxide layer, the interference pigment further comprises a second metal oxide layer that is formed between the inorganic substrate and the metal layer and that coats the inorganic substrate.

3. The interference pigment according to claim 1, wherein the metal is at least one selected from the group consisting of silver and gold.

4. The interference pigment according to claim 1, wherein the metal layer has an average thickness of 5 nm or less.

5. The interference pigment according to claim 1, wherein the metal layer has an average thickness of 2 nm or less.

6. The interference pigment according to claim 1, wherein, when the metal oxide layer that coats the metal layer is referred to as a first metal oxide layer, the first metal oxide layer is coated with a laminated layer comprising one or more transparent metal layers and one or more metal oxide layers that are laminated alternately.

7. A cosmetic comprising the interference pigment according to claim 1.

8. A paint comprising the interference pigment according to claim 1.

9. An ink comprising the interference pigment according to claim 1.

10. A resin composition comprising the interference pigment according to claim 1.

11. The interference pigment according to claim 1, wherein the material of the inorganic substrate is glass, the metal of the transparent metal layer is selected from the group consisting of silver and gold.

12. An interference pigment consisting of:
   a flaky inorganic substrate;
   a transparent metal layer that coats the inorganic substrate;
   a metal oxide layer that coats an outer surface of the transparent metal layer; and
   optionally a laminated layer that coats an outer surface of the metal oxide layer, consisting of one or more transparent metal layers and one or more metal oxide layers that are laminated alternately,
   wherein the material of the inorganic substrate is glass,
   the substrate has an average thickness of 0.1 μm to 10 μm,
   the metal of the transparent metal layer is at least one selected from the group consisting of silver and gold,
   the metal oxide layer has an average thickness of 80 nm to 350 nm, and
   the metal oxide layer includes 99 atom % or more of rutile titanium oxide.

13. An interference pigment consisting of:
   a flaky inorganic substrate;
   a second metal oxide layer that coats the inorganic substrate;
   a transparent metal layer that coats the second metal oxide layer;
   a first metal oxide layer that coats an outer surface of the transparent metal layer; and
   optionally a polyvalent metal compound layer coating the first metal oxide layer, the polyvalent metal compound layer consisting essentially of a hydroxide or hydrated oxide of at least one element selected from the group consisting of lanthanum, cerium, neodymium, and aluminum,
   wherein the material of the inorganic substrate is glass,
   the substrate has an average thickness of 0.1 μm to 10 μm,
   the metal of the transparent metal layer is at least one selected from the group consisting of silver and gold,
   the second and the first metal oxide layer has an average thickness of 80 nm to 350 nm, and
   the second and the first metal oxide layer includes 99 atom % or more of rutile titanium oxide.

* * * * *